United States Patent
Menhardt et al.

(10) Patent No.: US 12,372,545 B2
(45) Date of Patent: Jul. 29, 2025

(54) SYSTEM AND METHOD FOR DEVICE SPECIFIC QUALITY CONTROL

(71) Applicant: Beckman Coulter, Inc., Brea, CA (US)

(72) Inventors: Wido Menhardt, Los Gatos, CA (US); Thomas W. Roscoe, Prior Lake, MN (US); Takayuki Mizutani, Edina, MN (US)

(73) Assignee: Beckman Coulter, Inc., Brea, CA (US)

( * ) Notice: Subject to any disclaimer, the term of this patent is extended or adjusted under 35 U.S.C. 154(b) by 795 days.

(21) Appl. No.: 17/511,937

(22) Filed: Oct. 27, 2021

(65) Prior Publication Data
US 2022/0050121 A1 Feb. 17, 2022

Related U.S. Application Data

(63) Continuation of application No. PCT/US2020/030985, filed on May 1, 2020.

(30) Foreign Application Priority Data

May 6, 2019 (IN) .............................. 201941017982

(51) Int. Cl.
*G01N 35/00* (2006.01)
*G01N 21/76* (2006.01)
(Continued)

(52) U.S. Cl.
CPC ....... *G01N 35/00623* (2013.01); *G01N 21/76* (2013.01); *G06T 7/0004* (2013.01);
(Continued)

(58) Field of Classification Search
CPC ............. G01N 35/00623; G01N 21/76; G16H 40/20; G16H 10/40; G16H 50/70;
(Continued)

(56) References Cited

U.S. PATENT DOCUMENTS 6,067,466 A * 5/2000 Selker .................... A61B 5/349
600/513
9,877,655 B2 * 1/2018 Huang ................... G02B 23/26
(Continued)

FOREIGN PATENT DOCUMENTS

EP          0 353 591 B1     4/1996
WO     WO 2018/081617 A2     5/2018

OTHER PUBLICATIONS

International Search Report and Written Opinion dated Oct. 28, 2020 for International Application No. PCT/US20/30985, 11 pages.
(Continued)

*Primary Examiner* — Elias Desta
(74) *Attorney, Agent, or Firm* — FROST BROWN TODD LLP

(57) ABSTRACT

Quality control tests for a diagnostic instrument can be run in an efficient manner by using a subset of the potential quality control materials to perform tests for identifying failures in the diagnostic instrument's components. Such subsets could be defined in a variety of manners, and could allow component failures to be tested relatively more frequently in a more efficient manner. Additionally, issues for particular components of diagnostic instruments may be identified based on analysis of quality control results. This identification may be part of a method that comprises receiving a plurality of quality control results wherein each quality control result from the plurality of quality control results is obtained based on performing a measurement of a corresponding quality control sample using the diagnostic instrument.

21 Claims, 13 Drawing Sheets

(51) Int. Cl.
*G06T 7/00* (2017.01)
*G16H 10/40* (2018.01)
*G16H 40/20* (2018.01)
*G16H 40/40* (2018.01)
*G16H 50/70* (2018.01)
*H04N 23/90* (2023.01)

(52) U.S. Cl.
CPC ............. *G16H 10/40* (2018.01); *G16H 40/20* (2018.01); *G16H 40/40* (2018.01); *G16H 50/70* (2018.01); *H04N 23/90* (2023.01); *G06T 2207/30164* (2013.01); *G06T 2207/30168* (2013.01)

(58) Field of Classification Search
CPC ...... G16H 40/40; H04N 23/90; G06T 7/0004; G06T 2207/30164; G06T 2207/30168
See application file for complete search history.

(56) References Cited

U.S. PATENT DOCUMENTS

| | | |
|---|---|---|
| 2005/0174241 A1 | 8/2005 | Olsen |
| 2006/0292642 A1 | 12/2006 | Khosravi et al. |
| 2008/0169346 A1 | 7/2008 | Schad et al. |
| 2009/0075385 A1 | 3/2009 | Fournier et al. |
| 2009/0136386 A1 | 5/2009 | Duffy et al. |
| 2016/0356801 A1 | 12/2016 | Glavina et al. |
| 2019/0271713 A1 | 9/2019 | Heinemann et al. |

OTHER PUBLICATIONS

Berman, P et al. "Tight Approximability Results for Test Set Problems in Bioinformatics", Jun. 2004, 13 pages.

* cited by examiner

SYSTEM AND METHOD FOR DEVICE SPECIFIC QUALITY CONTROL

CROSS REFERENCE TO RELATED APPLICATIONS

This application is a continuation of International Application Number PCT/US20/30985, filed in the United States Patent Office on May 1, 2020, and titled "System and Method for Device Specific Quality Control," which is related to, and claims the benefit of, provisional application 201941017462, filed in the Indian patent office on May 2, 2019, and titled "System and Method for Device Specific Quality Control, and provisional application 201941017982, filed in the Indian patent office on May 6, 2019, and titled "System and Method for Improved Troubleshooting. The disclosures of each of those applications are hereby incorporated by reference in their entirety.

FIELD

The disclosed technology pertains to a system and method for identifying failures in clinical analyzers.

BACKGROUND

Clinical analyzers will use quality control materials and procedures to assure the accuracy of their results. For example, for a given assay, tests comprising measurements of corresponding quality control materials may be run several times per day and at several different concentrations. However, these quality control materials are costly, their analysis takes time, and the failures they indicate are often difficult to diagnose. Additionally, analyzers may employ sensors for process monitoring of clinical steps in the processing of quality control materials or patient tests. These may include sensors for temperature, pressure, imaging, voltage and/or capacitance. In some cases an analyzer may even have on-board diagnostic capabilities separate from its quality control measurements. However, even with these sensors, the data available may not provide specificity needed to pinpoint errors in an analyzer.

SUMMARY

There is a need for an improved system and method for troubleshooting of clinical analyzers in a manner that is efficient in its use of quality control materials. It may thus ben an object of some embodiments to provide a method that could comprise steps such as obtaining a set of assays used by a diagnostic instrument to evaluate samples, performing a first quality control test on the diagnostic instrument, and performing a second quality control test on the diagnostic instrument. In some such embodiments, the diagnostic instrument may comprise a plurality of components. In some such embodiments, the first quality control test on the diagnostic instrument may comprise determining if there has been a failure in an assay from the set of assays by performing steps comprising obtaining a first number of measurements. In some such embodiments, the first number of measurements may be obtained by, for each assay in the set of assays, measuring each sample in a set of samples of a quality control material corresponding to that assay. In some such embodiments, the second quality control test on the diagnostic instrument may comprise determining if there has been a failure in a component from the plurality of components by performing steps comprising obtaining a second number of measurements. In some such embodiments, the second number of measurements may be obtained by, for each assay in a subset of the set of assays, measuring at least one sample in the set of samples of the quality control material corresponding to that assay.

There is also a need for an improved system and method for troubleshooting of clinical analyzers and pinpointing failures or identifying incipient failures before they take place. It may thus be an object of some embodiments to provide a method that could comprise steps such as receiving a plurality of quality control results wherein each quality control result from the plurality of quality control results is obtained based on performing a measurement of a corresponding quality control sample using a diagnostic instrument that comprises a plurality of components, identifying an issue for a particular component from the plurality of components based on analysis of at least two quality control results from the plurality of quality control results, and executing a remediation action for the particular component based on identifying the issue for the particular component.

In some embodiments, the above objectives may be fulfilled by the subject matter of the independent claims, wherein further embodiments may be incorporated in the dependent claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
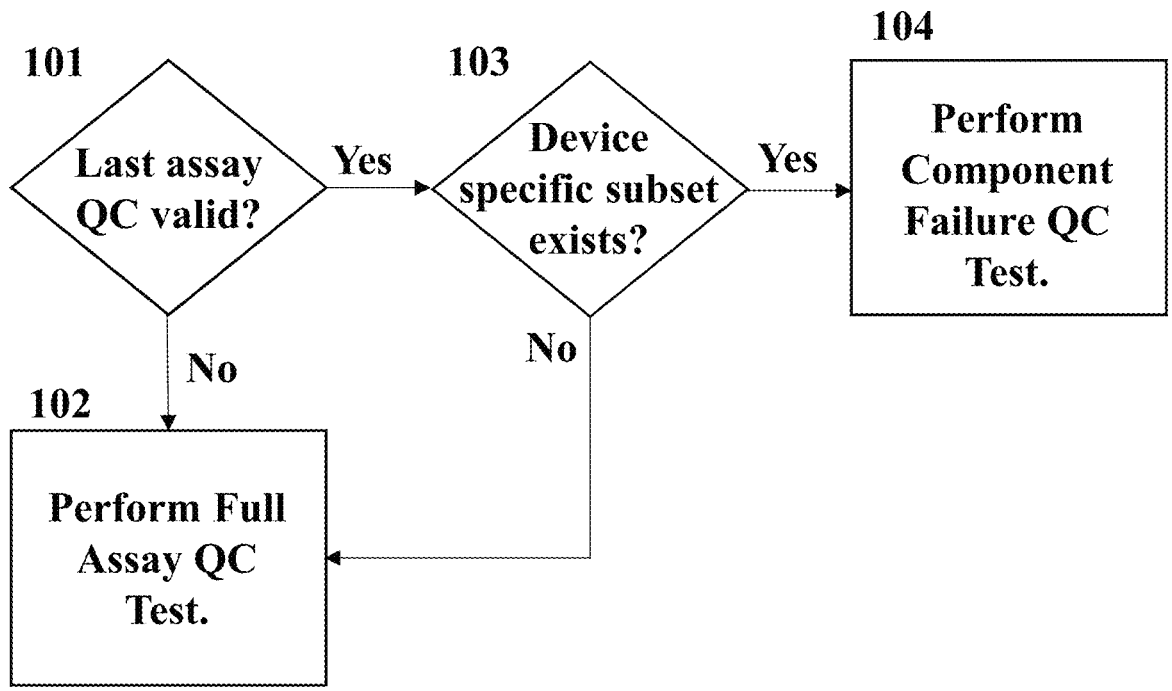
FIG. 1 illustrates a method that could be used to efficiently use quality control materials while testing an analyzer in a context where more frequent testing is necessary for device component failures than assay failures.

In light of the above, it could be beneficial to perform troubleshooting on a diagnostic instrument such as a clinical analyzer in a manner that is efficient in its use of quality control materials and/or that could pinpoint problems underlying failures of quality controls and/or that could identify incipient failures before they take place. According to a first aspect, some embodiments may include a method that could comprise steps such as performing a first test on the diagnostic instrument, and performing a second quality on the diagnostic instrument. In some such embodiments, the diagnostic instrument may comprise a plurality of components. In some such embodiments, the first test on the diagnostic instrument may comprise determining if there has been a failure in an assay from a set of assays used by the diagnostic instrument to evaluate samples by performing steps comprising obtaining a first number of measurements. In some such embodiments, the first number of measurements may be obtained by, for each assay in the set of assays, measuring each sample in a set of samples of a test material corresponding to that assay. In some such embodiments, the second test on the diagnostic instrument may comprise determining if there has been a failure in a component from the plurality of components by performing steps comprising obtaining a second number of measurements. In some such embodiments, the second number of measurements may be obtained by, for each assay in a subset of the set of assays, measuring at least one sample in the set of samples of the test material corresponding to that assay.

According to a second aspect, in some embodiments such as described in the context of the first aspect, the subset of the set of assays may have a cardinality different from a cardinality of the set of assays.

According to a third aspect, in some embodiments such as described in the context of the first aspect, the first test and the second test may both be quality control tests. In some such embodiments, each test material may be a quality control material.

According to a fourth aspect, some embodiments such as described in the context of the third aspect may comprise periodically performing quality control tests on the diagnostic instrument which comprise obtaining the first number of measurements. In some such embodiments, each quality control test on the diagnostic instrument that comprises obtaining the first number of measurements is separated from a most recent preceding quality control test on the diagnostic instrument that comprises obtaining the first number of measurements by at least a first period. In some such embodiments, the method may comprise periodically performing quality control tests on the diagnostic instrument which comprise obtaining the second number of measurements. In some such embodiments, each quality control test on the diagnostic instrument that comprises obtaining the second number of measurements is separated from a most recent preceding quality control test on the diagnostic instrument that comprises obtaining the second number of measurements by less than the first time period.

According to a fifth aspect, in some embodiments such as described in the context of the first aspect, the subset of the set of assays may be defined by using the plurality of components to model a universe for a problem, and generating an approximate solution for the problem. In some such embodiments, the problem may be the set cover problem and the minimum test collection problem.

According to a sixth aspect, in some embodiments such as described in the context of the fourth aspect, the approximate solution may be generated using a greedy algorithm.

According to a seventh aspect, in some embodiments such as described in the context of the fourth aspect, the problem may be the minimum test collection problem.

According to an eighth aspect, in some embodiments such as described in the context of the first aspect, the subset of the set of assays may be defined using a means for determining a component covering subset.

According to an ninth aspect, in some embodiments such as described in the context of the first aspect, for each assay in the set of assays, the set of samples of the test material corresponding to that assay may comprise a first sample having a first concentration of the test material, a second sample having a second concentration of the test material, and a third sample having a third concentration of the test material.

According to a tenth aspect, some embodiments may include a method comprising steps such as receiving a set of parameters wherein each parameter from the set of parameters is obtained based on performing a measurement of a corresponding sample using a diagnostic instrument that comprises a plurality of components, identifying an issue for a particular component from the plurality of components based on analysis of at least two parameters from the set of parameters, and executing a remediation action for the particular component based on identifying the issue for the particular component.

According to an eleventh aspect, in some embodiments such as described in the context of the tenth aspect, each parameter from the set of parameters may be related to quality control.

According to a twelfth aspect, in some embodiments such as described in the context of the tenth aspect, the set of parameters may comprise a failed quality control result outside an acceptance tolerance for the diagnostic instrument and a successful quality control result within the acceptance tolerance for the diagnostic instrument. In some such embodiments, identifying the issue for the particular component may be performed by determining that the particular component is a likely root cause for the failed quality control result. In some such embodiments, this determination may be based on determining that the corresponding sample for the failed quality control result was for an assay previously identified as susceptible to failures in the particular component, and determining that the corresponding sample for the successful quality control result was for an assay not previously identified as susceptible to failures in the particular component.

According to a thirteenth aspect, in some embodiments such as described in the context of the tenth aspect, each parameter from the set of parameters may be a quality control result. In some such embodiments, the set of parameters may not comprise any quality control results outside an acceptance tolerance for the diagnostic instrument, and identifying the issue for the particular component from the plurality of components may be performed based on identifying a pattern with the set of parameters.

According to a fourteenth aspect, in some embodiments such as described in the context of the thirteenth aspect, the diagnostic instrument may comprise a case and a set of one or more temperature sensors disposed inside the case. In some such embodiments, identifying the pattern with the set of parameters may comprise identifying a correlation between temperature data captured by the set of one or more temperature sensors and two or more parameters from the set of parameters whose corresponding samples were for an assay previously identified as susceptible to temperature control failures in the particular component.

According to a fifteenth aspect, in some embodiments such as described in the context of the thirteenth aspect, for each parameter from the set of parameters, the corresponding sample for that parameter may be a quality control sample. In some such embodiments, the diagnostic instrument may be configured to, for each quality control sample on which it performs a measurement, capture a test number for that quality control sample. In some such embodiments, identifying the pattern with set of parameters may comprise identifying a correlation between test numbers for parameters for assays previously identified as being hard to suspend (e.g., because they are sticky, or due to the presence of clamping antibodies) and parameters corresponding to samples for assays previously identified as being hard to suspend.

According to a sixteenth aspect, in some embodiments such as described in the context of the thirteenth aspect, the diagnostic instrument may comprise a luminometer and may be configured to capture substrate blank measurements comprising values obtained when vessels containing substrate adapted to generate chemiluminescent light in the presence of ALP are placed in the luminometer and measured without adding ALP. In some such embodiments, identifying the pattern with the set of parameters may comprise identifying a correlation between substrate blank measurements and parameters corresponding to samples for sandwich assays.

According to a seventeenth aspect, in some embodiments such as described in the context of the thirteenth aspect, the set of parameters may comprise a first quality control result, a second quality control result, and a third quality control result. In some such embodiments, the first quality control result may correspond to a quality control sample at a first concentration for an assay previously identified as susceptible to failures in the particular component. In some such embodiments, the second quality control result may correspond to a quality control sample at a second concentration for the assay previously identified as susceptible to failures in the particular component. In some such embodiments, the second concentration may be greater than the first concentrations. In some such embodiments, the third quality control result may correspond to a quality control sample at a third concentration for the assay previously identified as susceptible to failures in the particular component. In some such embodiments, the third concentration may be greater than the second concentration. In some such embodiments, identifying the pattern with the set of parameters may comprise calculating a projected result line for the assay previously identified as susceptible to failures in the particular component. In some such embodiments, this calculation may be based on the first quality control result, the second quality control result, a first expected value based on lower and upper signal levels for the quality control sample at the first concentration for the assay previously identified as susceptible to failures in the particular component, and a second expected value based on lower and upper signal levels for the quality control sample at the second concentration for the assay previously identified as susceptible to failures in the particular component. In some such embodiments, identifying the issue for the particular component may be performed by determining that the third quality control result does not match a value predicted based on lower and upper signal levels for the quality control sample at the third concentration for the assay previously identified as susceptible to failures in the particular component and the projected result line.

According to an eighteenth aspect, in some embodiments such as described in the context of the thirteenth aspect, the diagnostic instrument may comprise a wash wheel and a set of one or more cameras disposed proximate the wash wheel. In some such embodiments, identifying the pattern with the set of parameters may comprise identifying a correlation between parameters for samples corresponding to sandwich assays and grayscale values derived from images of vials containing the samples corresponding to the sandwich assays captured by the set of one or more cameras disposed proximate the wash wheel.

Corresponding systems comprising one or more computers configured by computer executable instructions stored on non-transitory computer readable media to perform steps of methods described in any of the preceding embodiments, as well as non-transitory computer readable media storing instructions for performing steps of method described in any of the preceding embodiments, could also be implemented without undue experimentation by those of ordinary skill in the art based on this disclosure. Accordingly, the preceding description of potential embodiments and aspects should be understood as being illustrative only, and should not be treated as limiting.

To illustrate how it may be possible to efficiently use quality control materials while testing an analyzer, consider a case where one or more components of an analyzer are likely to be subject to more frequent failures than the assays used by the analyzer in testing samples. In such a case, a regulation requiring a test of each failure mode when the risk of failure rises above a threshold amount (e.g., 5%) could require that component failure be tested for on a relatively more frequent basis than failures in assays (e.g., every eight hours versus every twenty four hours, which could roughly be translated into a test every shift versus a test every day). Accordingly, in such a situation, rather than measuring quality control materials for every assay used by the analyzer (a "Full Assay QC Test") whenever a quality control test was done, it would be more efficient if most tests only included only a subset of materials necessary to identify if there was a component failure (a "Component Failure QC Test"), while Full Assay QC Tests would only be run when necessary given the assays' relatively less frequent failures.

Turning now to the figures, FIG. 1 illustrates a method that could be used to efficiently use quality control materials while testing an analyzer in a context where more frequent testing is necessary for device component failures than assay failures. Initially, when running a quality control (QC) test using the method of FIG. 1, a check 101 could be made of whether the results of the most recent Full Assay QC Test were still valid. For example, if there was a policy that a Full Assay QC Test had to be run every twenty-four hours, then if the most recent Full Assay QC Test had taken place only eight hours earlier the check 101 could indicate that the results of that test were still valid. Alternatively, if the most recent Full Assay QC Test had taken place twenty hours earlier, and another quality control test wasn't expected to take place for more than four hours, then the check 101 could indicate that the results of the most recent Full Assay QC Test were not valid.

Where a check 101 such as described above indicates that the results of the last Full Assay QC Test were no longer valid, then the method of FIG. 1 could simply terminate with performing 102 a Full Assay QC Test. Alternatively, if the results of the last Full Assay QC Test were valid, then the method of FIG. 1 could proceed with checking 103 if there was a subset of the assays that could be subjected to QC testing to identify component failures without having to perform a Full Assay QC Test. This could be done, for example, by checking if the manufacturer of the analyzer in question had identified a subset of quality control materials that, if tested, would be sufficient to indicate if there was a component failure. Other approaches to performing this check 103 could be used in some embodiments. For example, in some cases, if no pre-defined subset of quality control materials had been defined, a laboratory could seek to generate one (e.g., using a method such as discussed below in the context of FIG. 2) and may only treat the check 103 as showing that no device specific subset exists if there was no predefined subset available and no subset could be dynamically generated. Other approaches (e.g., only relying on a predefined subset if it was associated with metadata showing that it had a created date more recent than the most recent change to the list of assays the analyzer was used to perform) are also possible and will be immediately apparent to those of ordinary skill in the art in light of this disclosure. Accordingly, the above description of checking 103 for whether a device specific subset exists should be understood as being illustrative only, and should not be treated as limiting.

However it is performed, if the check 103 indicated that no device specific subset existed, then the method of FIG. 1 could terminate with performing 102 a Full Assay QC Test. Alternatively, if the check 103 indicated that a device specific subset existed, then that subset of QC materials could be tested 104. If it indicated a failure, this could then trigger various remedial steps (e.g., scheduling a visit from a service engineer, providing an alert with instructions for the user regarding how the failure could be remediated, etc.). Alternatively, if no failures were indicated by the measurement 104 of the device specific subset this could be treated as an indication that all components of the analyzer were working properly, and the quality control test could be treated as successfully concluded.

Figure 2:
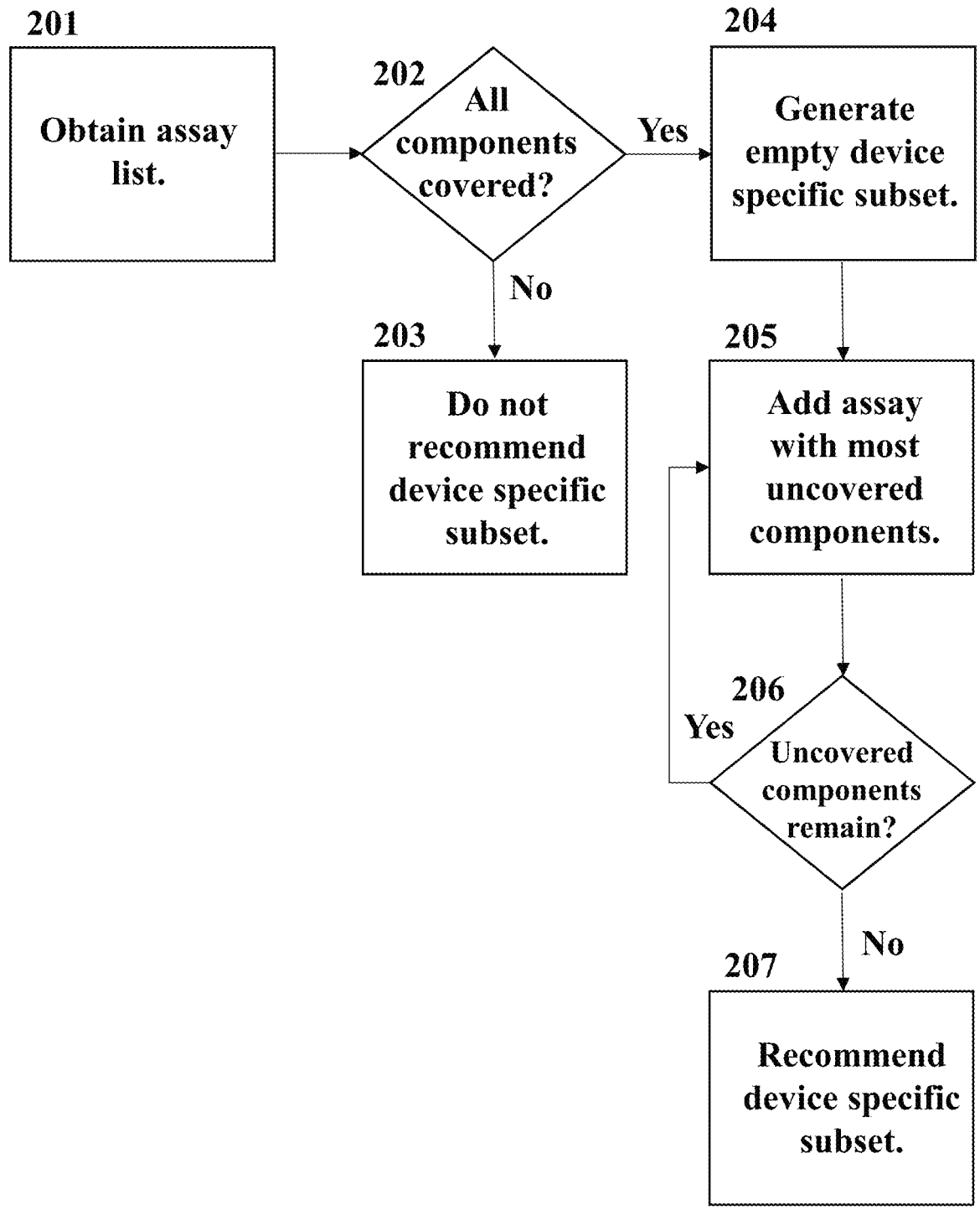
FIG. 2 illustrates a method that could be used to identify a subset of quality control materials that could be used to identify an analyzer component failure.

Turning now to FIG. 2, that figure illustrates a method that can be used to identify a subset of quality control materials that could be used to identify an analyzer component failure. Initially, in the method of FIG. 2, the entity identifying the subset of quality control materials would obtain 201 a list of the assays that would be used on the analyzer in question. This could be done in a variety of ways. For example, in cases where a method such as shown in FIG. 2 was being performed by the entity that would be operating the analyzer (e.g., a laboratory), obtaining 201 the list of assays could be performed by simply deciding what assays the analyzer would be used to perform. Alternatively, in a case where a method such as shown in FIG. 2 was being performed by an entity other than the entity that would be operating the analyzer (e.g., the analyzer's manufacturer, or a third party consultant), obtaining 201 the list of assays could be performed by asking the analyzer's operator what assays the analyzer would be used for. Other approaches (e.g., an assay vendor performing a method such as shown in FIG. 2 may be able to obtain 201 a list of assays by reviewing its sales records) are also possible and will be immediately apparent to those of ordinary skill in the art in light of this disclosure. Accordingly, the above description of obtaining 201 a list of assays should be understood as being illustrative only, and should not be treated as limiting.

Once the list of assays had been obtained 201, a method such as shown in FIG. 2 could proceed with checking 202 if the assays on the list covered all of the components of the analyzer. Like the step of obtaining 201 an assay list, the step of checking 202 if the assays on the list covered all of the components could be performed in a variety of ways. For example, in some cases, a component could be considered as "covered" if there was at least one assay that had been identified as susceptible to failures in that component. For instance, a competitive type assay could be treated as susceptible to failures in reagent delivery based on its sensitivity relative to sandwich assays, and so, in an embodiment where a component was treated as "covered" is there was an assay that had been identified as susceptible to its failure, a reagent delivery subsystem could be treated as "covered" if the list of assays included at least one competitive assay. As another example, in some cases a component would be treated as "covered" if there were assays that had both been identified as susceptible to failures in that component and assays that had not been so identified. In this type of scenario, if the list of assays included both a sandwich assay and a competitive assay, then the reagent delivery subsystem could be treated as "covered" based on the relative insensitivity of sandwich assays and the relative sensitivity of competitive assays to failures in that component. As another example, in some cases a particular component could be treated as "covered" if there was (1) a first assay that had been identified as sensitive to failures in the particular component; and (2) either (a) the first assay was not sensitive to failures in any other component or (b) for each other component whose failures the first assay was sensitive to, there was a set of other assays that included at least one assay that was both sensitive to failures in the particular component and not sensitive to failures in that other component. Other approaches (e.g., a component is considered to be "covered" if there are sufficient assays that are sensitive to failures in that component that failures in each of those assays could be treated as establishing a likelihood of failure in the component that is greater than some threshold probability) will be immediately apparent to those of ordinary skill in the art, and could be implemented in various embodiments. Accordingly, the discussion above of determining if a component is "covered" and the corresponding check 202 of whether all components are "covered" by the assay list should be understood as being illustrative only, and should not be treated as limiting.

Continuing with the discussion of FIG. 2, in some embodiments, if the check 202 indicated that not all components were covered by the assay list, the method could terminate by simply declining 203 to recommend any subset of quality controls that should be used when checking for component failures (which, in some embodiments, could result in all quality control tests being run as Full Assay QC Tests). Alternatively, if the check 202 confirmed that all components were covered by the complete assay list, then a process such as shown in FIG. 2 could proceed to determine a subset of the assays that would cover the components while not (necessarily) including all of the quality control materials that would be used in a Full Assay QC Test. This could begin by, for example, generating 204 an empty device specific subset—e.g., by instantiating a new array, vector, list or other data structure that would be used to hold the assays for the subset.

Once an empty device specific subset had been generated 204, its population could begin by adding 205 the assay with the most uncovered components. In various embodiments, this could be done in various ways. For example, in an embodiment where a component was considered to be "covered" if there was at least one assay that had been identified as susceptible to failures in that component, the assay that had been identified as susceptible to failures in the most components that were not already covered by assays in the subset (which, in the initial iteration, would simply be the assay identified as susceptible to failures in the most components) could be added 205 to the subset. Alternatively, in embodiments where an assay would be treated as "covered" based on relationships between multiple assays, the assay that contributed to the relationships for the largest number of assays could be added 205. For example, in an embodiment where a component would be treated as "covered" when there were enough assays identified as susceptible to failures in that component that quality control failures for each of those assays would establish a probability of failure in the component greater than a threshold probability, the assay that had been identified as susceptible to failures in the largest number of components that weren't already covered could be added 205 to the subset even though adding that assay may not result in any additional components crossing the threshold and therefore being "covered." Other approaches could be deployed in various embodiments, and will be immediately apparent to those of ordinary skill in the art in light of this disclosure. Accordingly, the description above of adding 205 the assay with the most uncovered components should be understood as being illustrative only, and should not be treated as limiting.

Continuing with the discussion of FIG. 2, after the assay with the most uncovered components had been added 205, a check 206 could be made of whether any uncovered components remained. This check 206 could be done in the same manner as the previous check 202 of whether all of the components were covered by the assay list, except instead of evaluating coverage against the entire assay list, this later check 206 would evaluate coverage against only those assays that had already been added 205 to the device specific subset. If the check 206 indicated that there were still components that had not been covered, then the process of FIG. 2 could add 205 the assay with the most components that were still uncovered, and could continue to iterate until a device specific subset had been identified that covered all components of the analyzer. Alternatively, when the check 206 indicates that all components had been covered, the process of FIG. 2 could terminate by recommending 207 the identified subset of devices (e.g., by displaying it on an output interface, storing it in an output file, storing it in memory to be used automatically for the next round of quality control testing intended to identify component failures, etc.).

Figure 3:
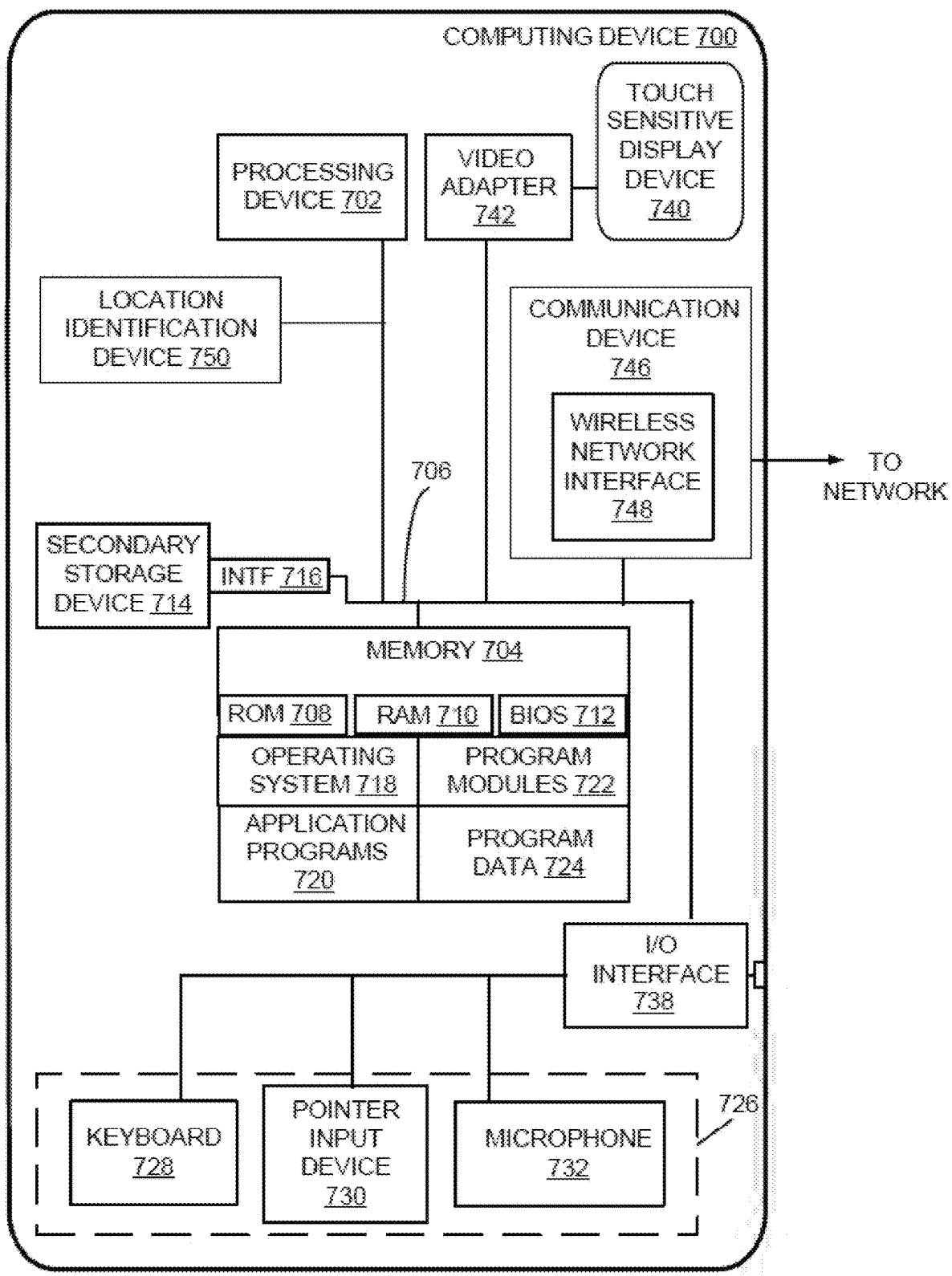
FIG. 3 illustrates an exemplary architecture of a computing device that can be used to implement aspects of the present disclosure.

Turning now to FIG. 3, that figure illustrates an exemplary architecture of a computing device that can be used to implement aspects of the present disclosure, including by performing methods such as shown in FIG. 1 and/or FIG. 2. As shown in FIG. 3, a computing device 700 may include, in some embodiments, at least one processing device 702, such as a central processing unit (CPU). A variety of processing devices are available from a variety of manufacturers, for example, Intel or Advanced Micro Devices. In this example, the computing device 700 also includes a system memory 704, and a system bus 706 that couples various system components including the system memory 704 to the processing device 702. The system bus 706 is one of any number of types of bus structures including a memory bus, or memory controller; a peripheral bus; and a local bus using any of a variety of bus architectures.

Examples of computing devices include a desktop computer, a laptop computer, a tablet computer, a mobile device (such as a smart phone, an iPod® mobile digital device, or other mobile devices), or other devices configured to process digital instructions. In some embodiments, a computing device's system memory 704 may include read only memory 708 and random access memory 710. A basic input/output system 712 containing the basic routines that act to transfer information within computing device 700, such as during start up, is typically stored in the read only memory 708.

In some embodiments, a computing device 700 may also include a secondary storage device 714 in some embodiments, such as a hard disk drive, for storing digital data. The secondary storage device 714 is connected to the system bus 706 by a secondary storage interface 716. The secondary storage devices and their associated computer readable media provide nonvolatile storage of computer readable instructions (including application programs and program modules), data structures, and other data for the computing device 700.

Although some embodiments may employ a hard disk drive as a secondary storage device, other types of computer readable storage media may be used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 714 or memory 704, including an operating system 718, one or more application programs 720, other program modules 722, and program data 724. In some embodiments, computing device 700 includes input devices to enable a user to provide inputs to the computing device 700. Examples of input devices 726 include a keyboard 728, pointer input device 730, microphone 732, and touch sensitive display 740. Other embodiments include other input devices 726. The input devices are often connected to the processing device 702 through an input/output interface 738 that is coupled to the system bus 706. These input devices 726 can be connected by any number of input/output interfaces, such as a parallel port, serial port, game port, or a universal serial bus. Wireless communication between input devices and interface 738 is possible as well, and includes infrared, BLUETOOTH® wireless technology, WiFi technology (802.11a/b/g/n etc.), cellular, and/or other radio frequency communication systems in some possible embodiments.

In some embodiments, a touch sensitive display device 740 may also be connected to the system bus 706 via an interface, such as a video adapter 742. The touch sensitive display device 740 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 740, the computing device 700 can include various other peripheral devices (not shown), such as speakers or a printer. The computing device 700 further includes a communication device 746 configured to establish communication across the network. In some embodiments, when used in a local area networking environment or a wide area networking environment (such as the Internet), the computing device 700 is typically connected to the network through a network interface, such as a wireless network interface 748. Other possible embodiments use other wired and/or wireless communication devices. For example, some embodiments of the computing device 700 include an Ethernet network interface, or a modem for communicating across the network. In yet other embodiments, the communication device 746 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The computing device 700 typically includes at least some form of computer-readable media. Computer readable media includes any available media that can be accessed by the computing device 700. By way of example, computer-readable media include computer readable storage media and computer readable communication media. Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 700.

Figure 4:
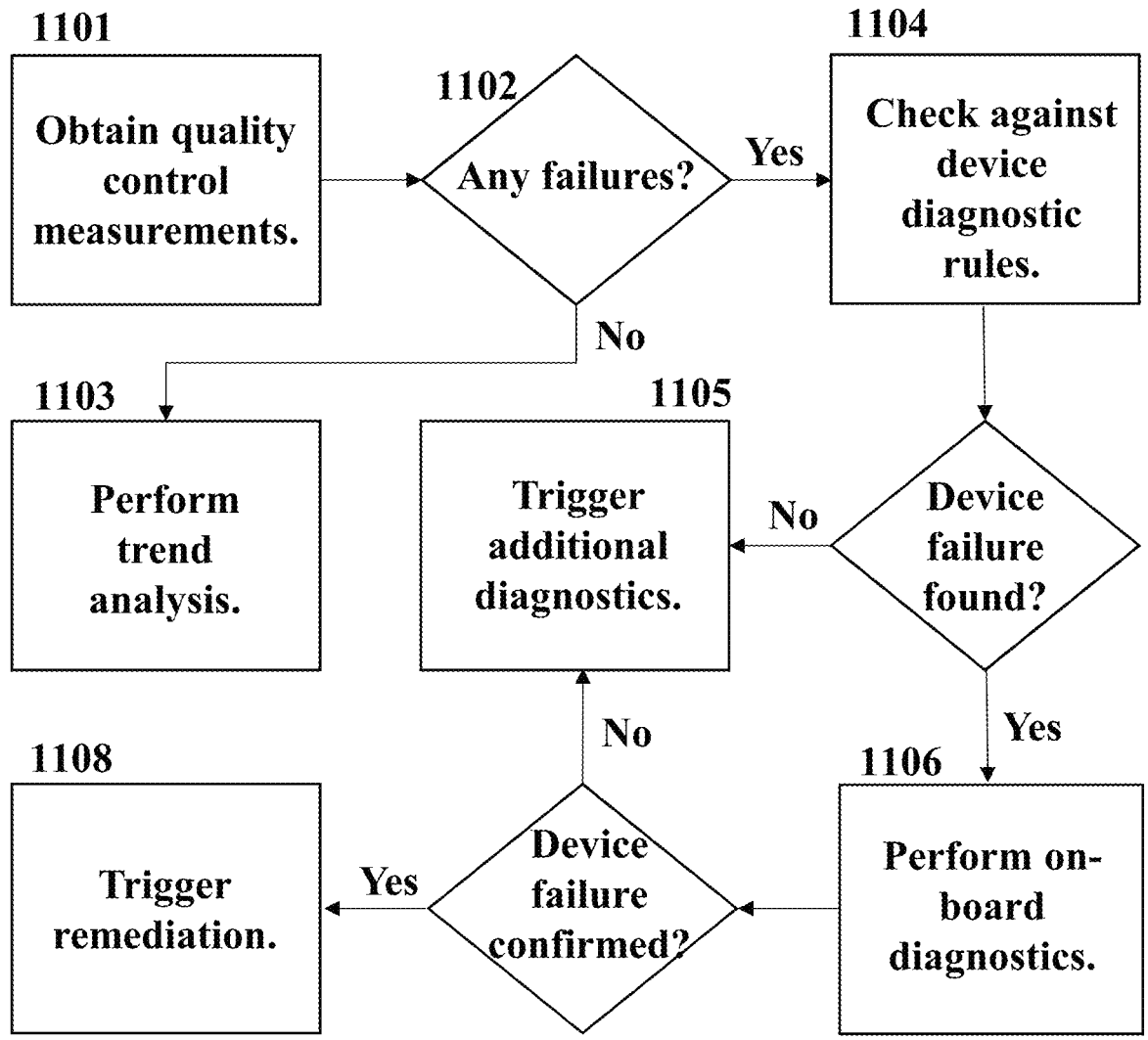
FIG. 4 illustrates a method that can be used to identify root causes of failures in some embodiments.

Turning now to FIG. 4, that figure illustrates a method that can be used to identify root causes of failures in some embodiments. Such a method could begin with obtaining 1101 quality control measurements. This could be done, for example, by running quality control tests on quality control materials corresponding to each of the assays an analyzer would perform on patient samples, and then storing the results of those tests in a memory.

Once they had been obtained, the test results of the quality control materials could be checked 1102 if any of them indicated a failure. For example, if one of the tests provided a measurement value that differed from an expected measurement value by more than a threshold amount, then this difference could be treated as indicating a failure in need of remediation. If there were no failures identified, then the analyzer could be returned to service in performing assays on patient samples or, in some embodiments, the test results could be used for trend analysis 1103 (which could also be referred to as pattern analysis), such as via methods of the types shown in FIGS. 5, 10-11 and 13.

Alternatively, if the test results of the quality control materials indicated that there was a failure, then a process such as shown in FIG. 4 could proceed with a root cause analysis by checking 1104 the failures against a set of device diagnostic rules. These device diagnostic rules could encode relationships between different types of quality controls and different components of the analyzer whose failure could impact those quality controls' test results. For example, to reflect that sandwich assays are relatively insensitive to reagent delivery (because for sandwich assays it can be expected that there will be enough antibodies delivered that there will be an excess of what is needed for a reaction even if there is an issue with reagent delivery), device diagnostic rules could include a rule stating that if quality control test results for multiple competitive type quality controls indicated there was a problem, while quality control test results for multiple sandwich type quality controls indicated there was not a problem, then this could be treated as indicating that there was a problem with the analyzer's reagent delivery subsystem, since reagent delivery problems would be more likely to impact results for the competitive than the sandwich assays. As another example, in some embodiments, an analyzer may be configured to maintain data regarding components that are used in a test (e.g., in an analyzer with multiple reagent pipettors, which reagent pipettor was used in a particular quality control test). In this type of embodiment, the device diagnostic rules may include a rule that if results of quality control tests performed using a particular component consistently indicated quality control failures, while results of quality control tests that did not utilize that component did not indicate failures, this should be treated as an indication that there was a failure in that particular component.

After any failed quality control test results had been checked 1104 against the device diagnostic rules, if the rules did not indicate there was a device failure underlying one or more of the test results, this could trigger additional diagnostic steps 1105, such as repeating the quality control test with a new vial from the same lot, or repeating the quality control test with a new vial from a different lot (but still containing the same quality control material). It is also possible that, in some cases, an analyzer's on-board diagnostic functionality (if any) may be invoked if the quality control test results were not sufficient to identify a root cause for one or more failed quality control tests. For example, in some embodiments, a method such as shown in FIG. 4 may be performed with an analyzer that is loaded with specialized diagnostic reagents (e.g., reagents comprising an elevated concentration of paramagnetic particles but lacking an antibody component), and the analyzer could be configured to execute self diagnostic routines in which machine vision analysis could be applied to digital camera images of the results of performing various processing steps with the specialized diagnostic reagent (e.g., a greyscale image of a reaction vessel with a mixture of the diagnostic reagent and a predetermined volume of wash buffer could be compared with expected brightness values to determine if there was a fault in the analyzer's resuspension functionality). Other additional diagnostic steps (e.g., dispatching a field service engineer in the event a root cause can't be determined after one or more rounds of additional diagnosis) are also possible and will be immediately apparent to those of ordinary skill in the art, and so the additional diagnostic steps described above should be understood as being illustrative only, and should not be treated as limiting.

Alternatively, if the device diagnostic rules indicated that an issue with one of the analyzer's components was the root cause of one or more failed quality control tests, then the analyzer's on-board diagnostics (if any) could be performed 1106 to confirm the root cause identification made using the diagnostic rules. After the on-board diagnostics had been performed 1106, if they did not detect a failure in the component identified as a root cause using the device diagnostic rules, then a method such as shown in FIG. 4 could perform some additional diagnostic steps 1105 of the type described previously. Otherwise, the confirmation of the component of the analyzer as a root cause of at least some of the quality control failures could be used to trigger 1108 remediation targeted at that component. This remediation could include, for example, automated remediation that could be performed by the analyzer itself (alignment correction of the type described in the context of FIGS. 6-9), or automatically generating a service call that would include the failure information and dispatch a field service engineer to the analyzer so that he or she could fix the component identified as the root cause of the failures. Of course, it should be understood that other approaches to remediating issues with components identified as root causes of quality control failures (e.g., presenting a user of the analyzer with instructions on actions he or she could take to adjust or replace the component in question) are also possible, and could be implemented by those of ordinary skill in the art without undue experimentation in light of this disclosure. Accordingly, the above description should be understood as being illustrative only, and should not be treated as implying limitations on the protection provided by this or any related document.

Figure 5:
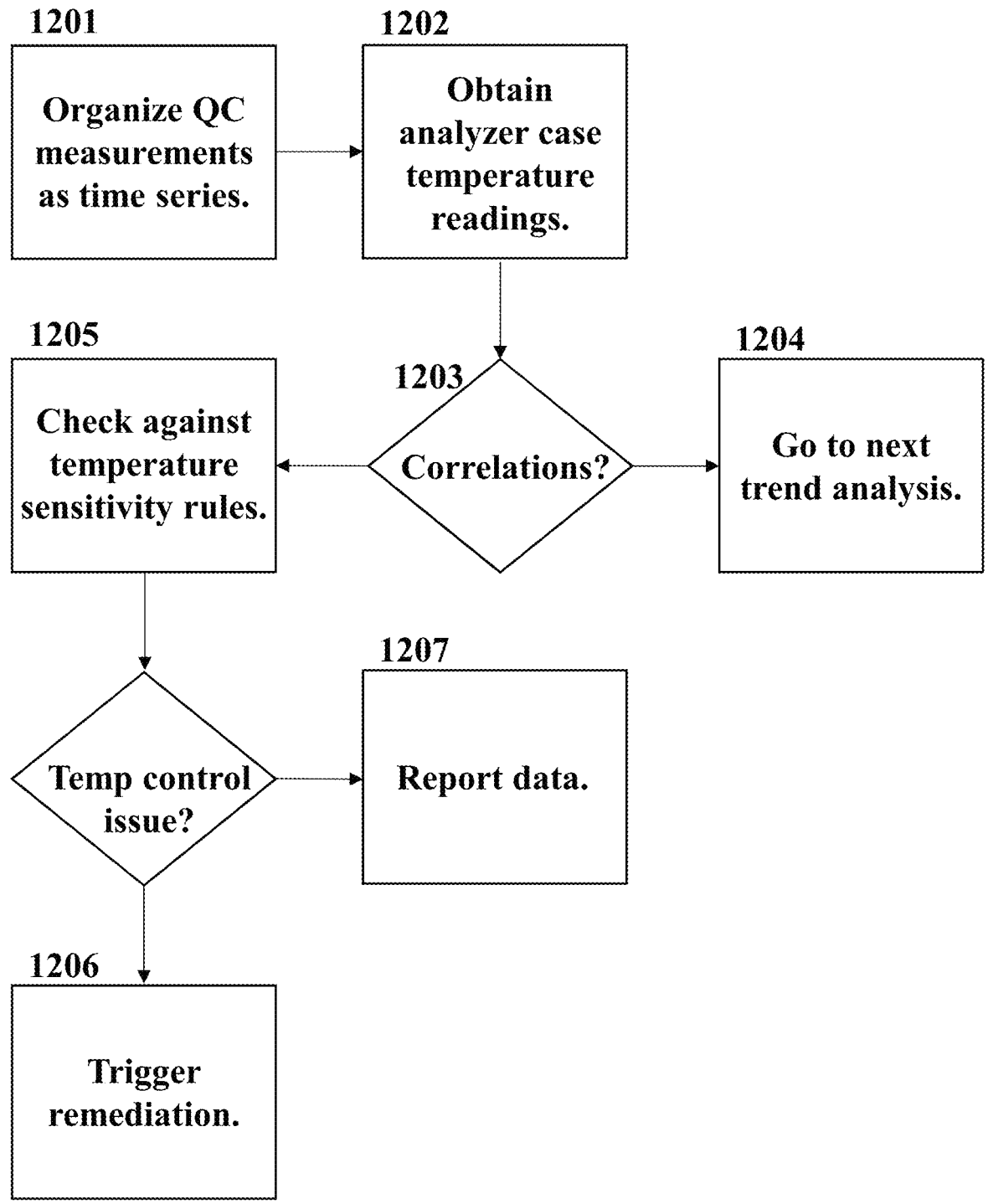
FIG. 5 illustrates a trend analysis method that can be used to check for incipient failures in an analyzer using temperature data.

Turning now to FIG. 5, that figure illustrates a trend analysis method that can be used to check for incipient failures in an analyzer using temperature data. Initially in the method of FIG. 5, quality control measurements (e.g., such as may be obtained through repeated performance of a process as shown in FIG. 4) could be organized 1201 into a time series (i.e., chronologically). Next, case temperature readings for the analyzer could be obtained 1202. This could be done, for example, by querying a database for temperature readings that had previously been made by a temperature sensor disposed inside the analyzer's case. These quality control and temperature measurements could then be tested 1203 to determine if there were any correlations between them. For example, if it appeared that at least a threshold amount (e.g., 5%) of variation in quality control measurements for a particular assay type could be attributed to changes in temperature (e.g., the signal strength for the particular assay type varied with the temperature), then this relationship could be treated as a correlation between that particular assay type and the temperature measured inside the analyzer's case. If no such correlations existed, a process such as shown in FIG. 5 could proceed 1204 with further trend analysis (e.g., trend analysis as illustrated in FIGS. 10-13). Alternatively, if a correlation was observed, then data could be subjected to further analysis to determine if it indicated an incipient failure of some aspect(s) of the analyzer's temperature control functionality.

If a correlation between quality control measurements and case temperature is identified, in some embodiments, that correlation could be checked 1205 against temperature sensitivity rules. In some embodiments, just as the device diagnostic rules discussed in the context of FIG. 4 could reflect relationships between quality control assays and components of an analyzer that would be used in testing those assays, temperature sensitivity rules could reflect relationships between quality control assays and components of an analyzer whose temperature was known to impact those assays' results. For example, there could be a rule stating that if there was a correlation between case temperature and quality control results of an assay that was sensitive to reagent pipettor temperature (e.g., because it had a dilution process), but no correlation between case temperature and quality control results of assays that were not sensitive to reagent pipettor temperature, this should be treated as an indication of an incipient failure of the reagent pipettor's temperature control system.

If the checking 1205 of temperature correlations with quality control results indicated that there was a temperature control issue, then a process such as shown in FIG. 5 could proceed with remediation 1206 of that issue (e.g., triggering a service call in which a field service engineer would be dispatched to the location of the analyzer along with information indicating the temperature control components where the incipient failure had been detected). Alternatively, if the checking 1205 did not identify a temperature control issue, the data in which the correlation was identified could be reported 1207 to a central location (e.g., a data center maintained by the manufacturer of the analyzer being tested) where it could be stored and subsequently analyzed to determine if the temperature sensitivity rules should be updated (e.g., if a temperature control component of the analyzer subsequently fails, data from the analyzer, as well as other analyzers, could be checked to determine if the unknown correlation was actually a useful predictor of problems with the temperature control component that subsequently failed).

Figure 10:
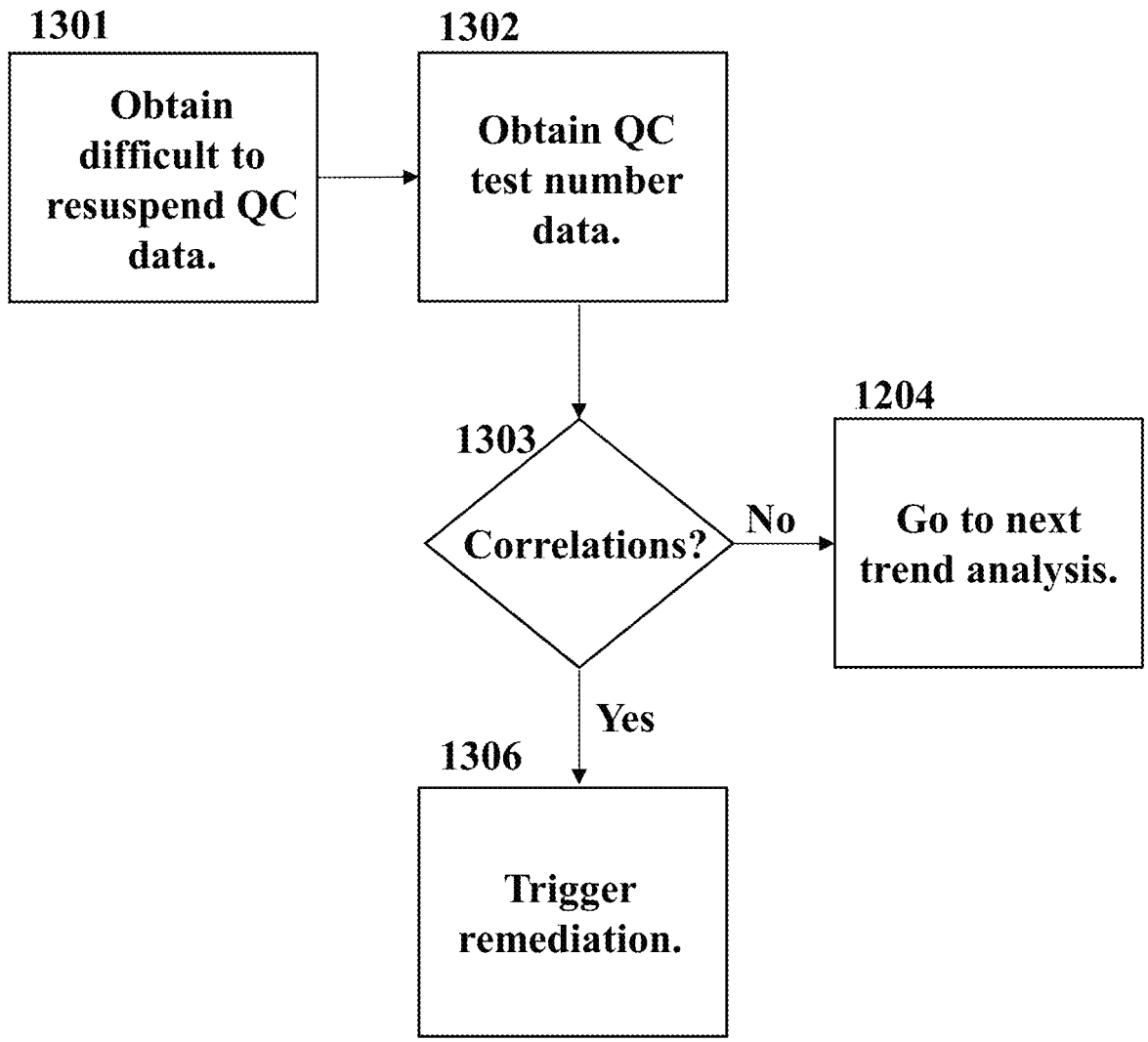
FIG. 10 illustrates a trend analysis method that can be used to check for incipient failures in an analyzer using data showing test number within a reagent pack.

Turning now to FIG. 10, that figure illustrates a trend analysis method that can be used to check for incipient failures in an analyzer using data showing test number within a reagent pack. Initially, a trend analysis method such as shown in FIG. 10 could obtain 1301 quality control ("QC") data for assays with that were difficult to resuspend (e.g., vitamin B12 assays, which are known to have sticky particles). This could be done, for example, by querying a database with quality control measurements information to retrieve time series for quality control tests done with assays having particles previously identified as being difficult to resuspend. Next, a process such as shown in FIG. 10 could proceed by obtaining 1302 quality control test number data corresponding to the measurements for the assays with sticky particles. This could be done in a variety of manners. For example, in some embodiments, an analyzer may be configured to capture the test number of an assay in a reagent pack when performing a quality control test. In this type of embodiment, when a quality control measurement is stored (e.g., in a database as described previously), it could be stored along with the number from the reagent pack of the assay that was tested to generate the measurement result. With this type of information stored, a method such as shown in FIG. 10 could obtain 1302 the test number data as part of the query for obtaining 1301 difficult to resuspend particle time series data (e.g., the time series data could be retrieved in the form of a set of records, each of which would include both a measurement and the number of the assay that was tested to generate that measurement).

After the measurements and numbers for the tests in the reagent packs been obtained 1301 1302, the measurements could be tested 1303 for correlations, and in particular for relationships in which lower signals for the QC measurements correlated with lower numbers for tests in the reagent packs. If no correlations were identified, then a method such as shown in FIG. 10 could proceed 1204 with further trend analysis (e.g., as discussed in the context of FIGS. 11-13). Otherwise, if a correlation was identified, then this could trigger 1306 remediation, for example, by dispatching a field service engineer to replace or adjust the ultrasonic probe that would be used by the analyzer for resuspension.

Figure 11:
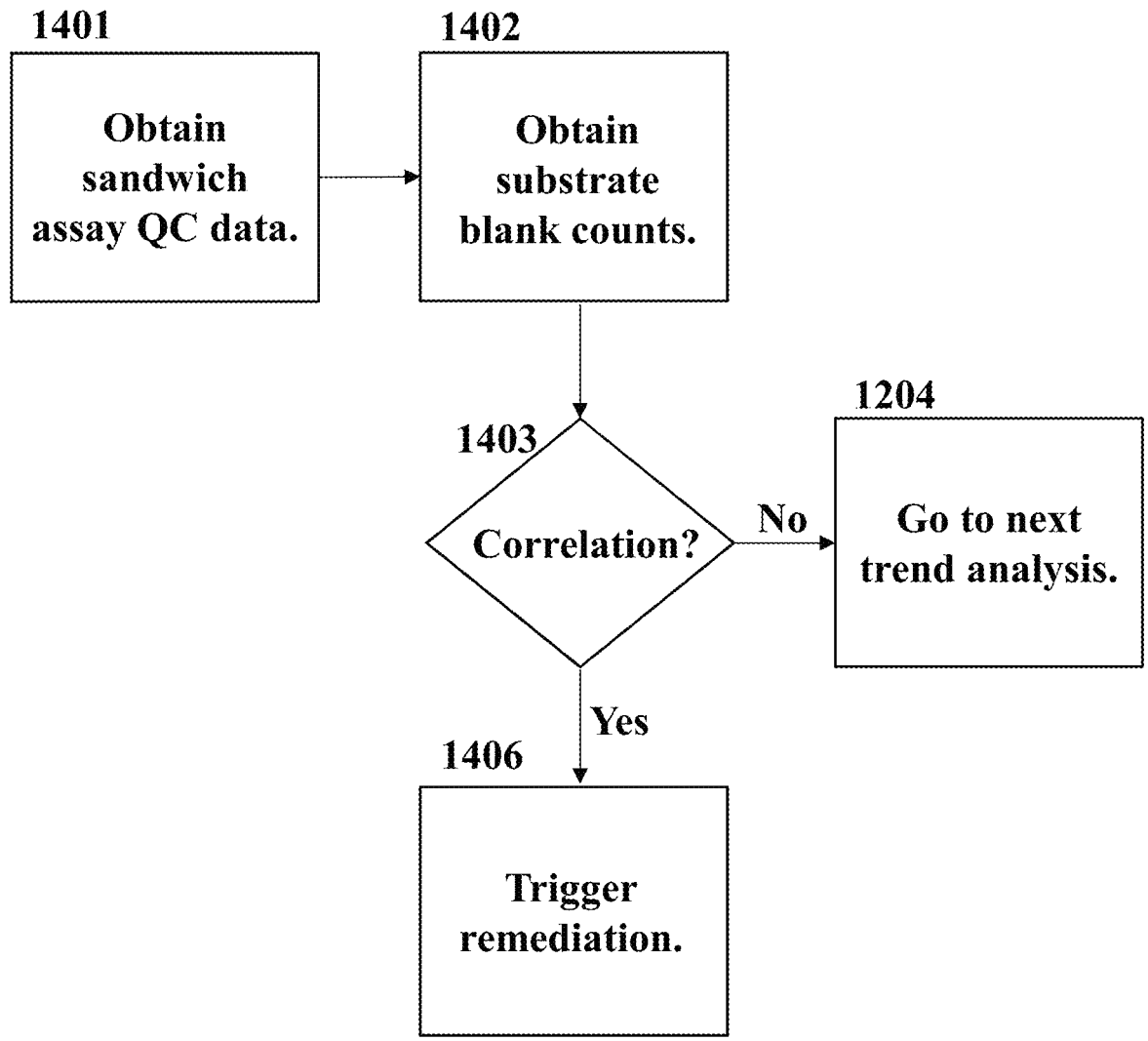
FIG. 11 illustrates a trend analysis method that can be used to check for incipient failures in an analyzer using substrate blank counts.

Turning now to FIG. 11, that figure illustrates a trend analysis method that can be used to check for incipient failures in an analyzer using substrate blank counts.

As shown in FIG. 11, this type of trend analysis could begin with obtaining 1401 sandwich assay QC data (e.g., by performing a database query for results of tests performed on sandwich assay QC materials). The method could also include obtaining 1402 substrate blank counts. This could be done, for example, by repeatedly performing substrate blank checks (e.g., by adding substrate adapted to generate chemiluminescent light in the presence of alkaline phosphatase into a plurality of vessels (e.g., ten vessels), incubating the vessels as if they were being used in an assay (e.g., incubating for 48 seconds), and then using a luminometer to detect luminance in each of the vessels after it had been incubated and/or by retrieving results of a laboratory's daily substrate blank checks done prior to analysis of patient samples), adding the results of those substrate blank checks to a database along with date information showing when the substrate blank checks were performed, then retrieving that information from the database when it was time to obtain 1402 the substrate blank counts. The sandwich assay QC data and substrate blank counts could then be checked 1403 for correlations. If it appeared that such a correlation existed, this could be treated as indicating that an incipient failure was likely in either the analyzer's substrate dispenser or its luminometer, which could in turn trigger 1406 remediation of the type described previously for those components. Alternatively, if no correlations were found, a method such as shown in FIG. 11 could go to 1204 the next trend analysis (e.g., trend analysis such as described in the context of FIGS. 12 and 13).

Figure 12:
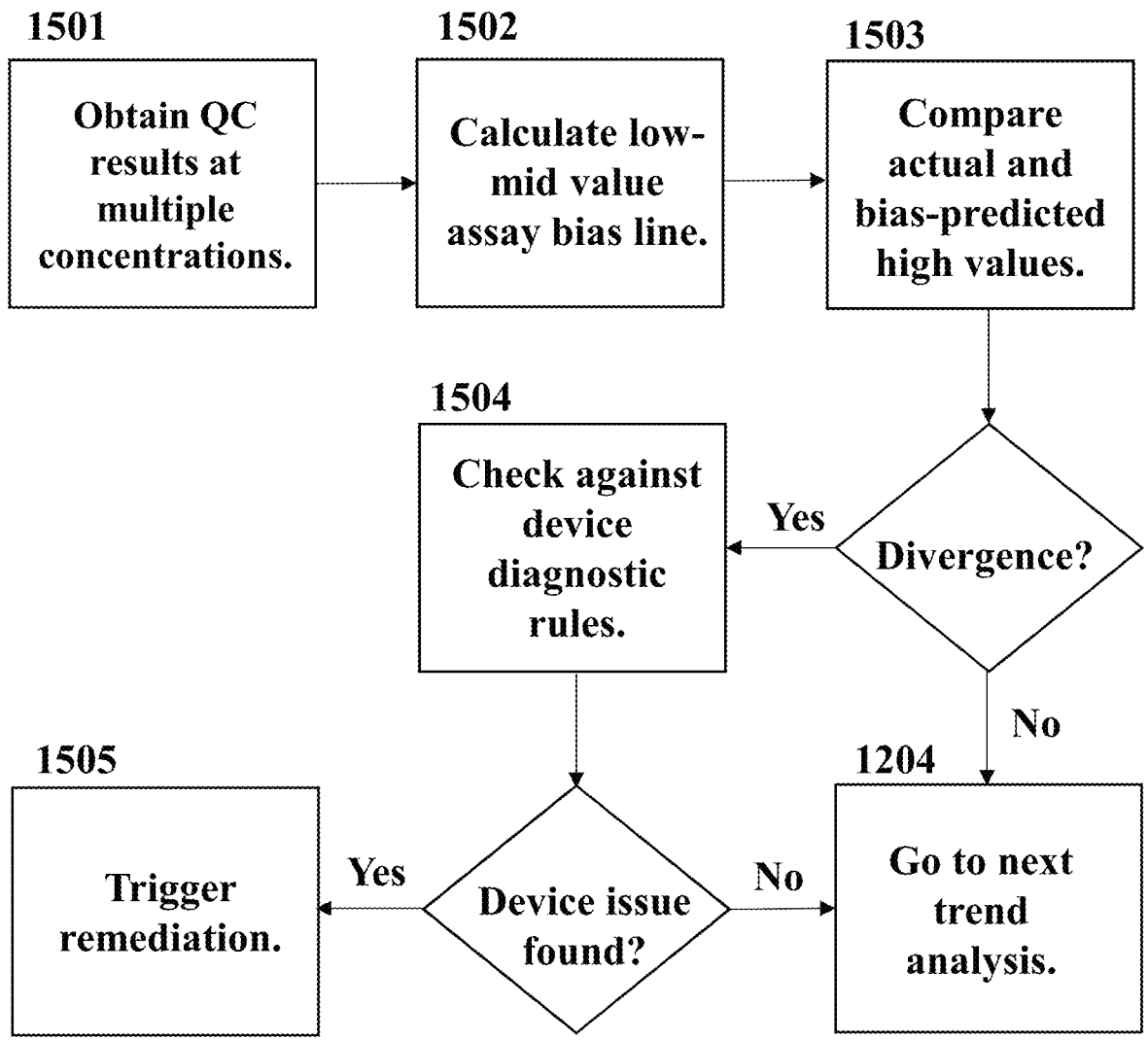
FIG. 12 illustrates a trend analysis method that can be used to identify issues using slopes of quality control data points.

Turning now to FIG. 12, that figure illustrates a trend analysis method that can be used to identify issues using slopes of QC data points. As shown in FIG. 12, such a method could begin with obtaining 1501 QC results at multiple concentrations. This could be done, for example, by performing tests on QC materials having multiple concentrations, storing those results in a database, and retrieving them (or a subset of them, such as results for sandwich assays) with a database query when the time came to obtain 1501 the QC results. Next, these results can be used to calculate 1502 a low to mid value assay bias line. This calculation can be done, for example using steps such as:

1) determine an expected QC low concentration result, which, in various embodiments, may be done by simply retrieving an average QC low concentration value provided by a vendor, or by calculating an expected QC low concentration result by averaging vendor supplied lower signal limit (LSL) and upper signal limit (USL) values for the low concentration QC material;
2) determine an expected QC mid concentration result, e.g., using a vendor supplied value or by averaging values as described above in the context of the expected QC low concentration result; and
3) generate the expected bias line by treating the expected and actual low and mid concentration results as data points and interpolating between them.

Figure 14:
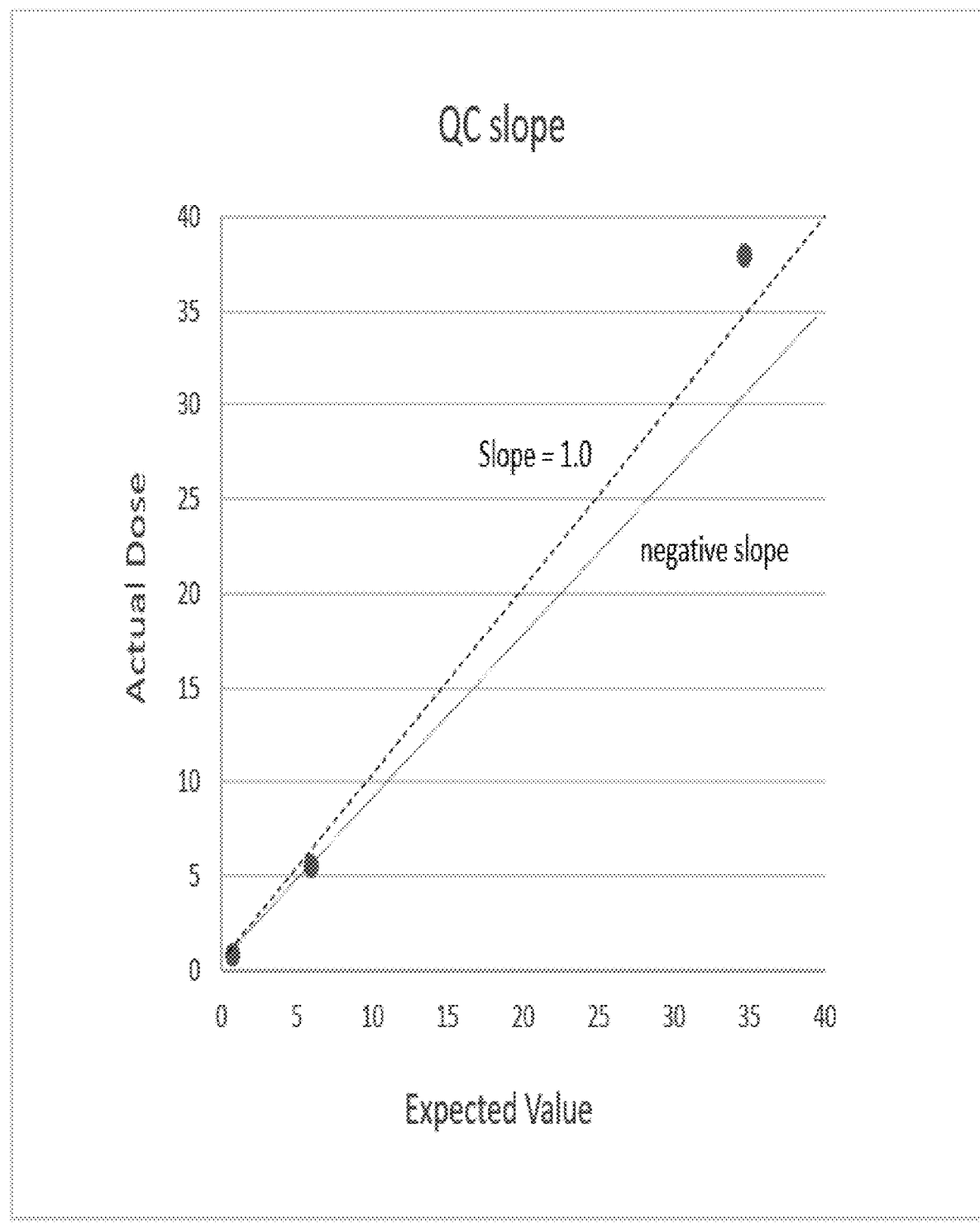
FIG. 14 illustrates a relationship in which an expected value (e.g., a value assigned by a vendor) and an actual value for a high concentration quality control material diverge from each other.

After the low-mid value assay bias line had been calculated 1502, the test result value for the high concentration QC material can be compared 1503 with the result that would have been expected based on the bias line given the USL and LSL values for the high concentration QC material. For example, as shown in FIG. 14, the test results that would have been expected for a high concentration QC material for a TSH assay based on it having LSL and USL values shown in table 1, and on the low and mid concentration quality control materials for that assay having the actual, LSL and USL values shown in table 1, would be different than the actual test value for the high concentration QC material shown in table 1.

TABLE 1

| TSH | QC1 | QC2 | QC3 |
|---|---|---|---|
| LSL | 0.630 | 4.990 | 29.600 |
| USL | 0.831 | 6.850 | 39.700 |
| Mean | 0.731 | 5.920 | 34.650 |
| Actual | 0.824 | 5.513 | 37.943 |

In cases where this type of comparison revealed no divergence, then the process could proceed 1204 with the next trend analysis. Alternatively, in cases where there is a divergence, the divergence could be checked 1504 against device diagnostic rules in a manner similar to that described previously for FIG. 4. For example, assays whose QC results showed divergences could be treated as equivalent to failed test results, and cross-assay comparisons of the type described in the context of FIG. 4 could be applied to identify specific components of the analyzer that may be at risk for incipient failure. If such a device issue was identified, then it could be remediated 1505, either directly or after confirmation with on-board diagnostics such as described in the context of FIG. 4. Alternatively, if no such incipient failure risks were identified, the process could proceed with next trend analysis 1204.

Figure 13:
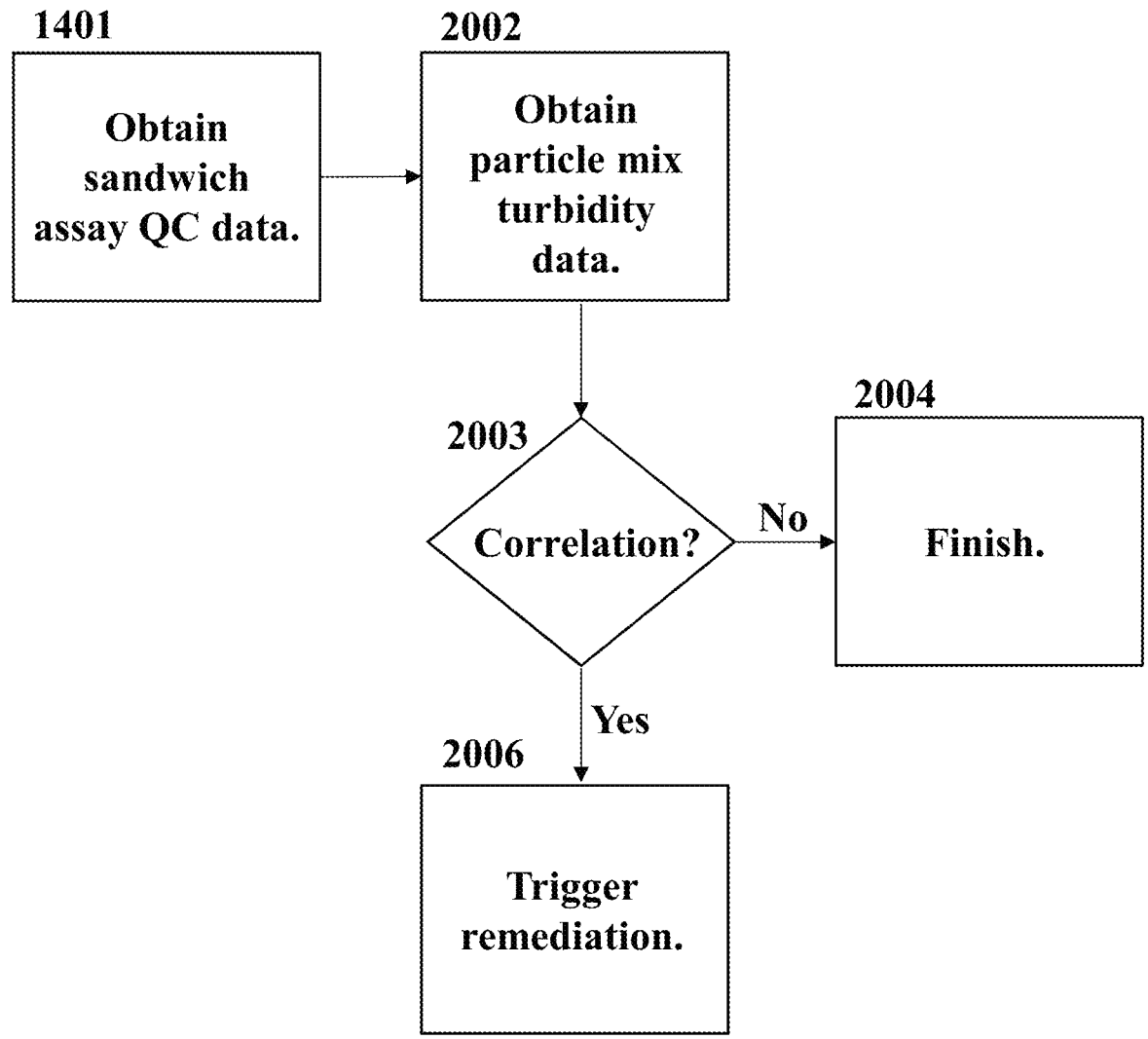
FIG. 13 illustrates a trend analysis method that can be used to identify issues using particle mix turbidity data.

Turning now to FIG. 13, that figure illustrates a trend analysis method that can be used to identify issues using particle mix turbidity data. A method such as shown in FIG. 13 could begin in a manner similar to that described in the context of FIG. 11 by obtaining 1401 sandwich assay QC data. Next, the method could proceed by obtaining 2002 particle mix turbidity data. This could be done, for example, by positioning one or more cameras proximate to a wash wheel of the analyzer and capturing images of reaction vessels after the QC assays had been added at various points in an analytic process (e.g., both before and after substrate has been added to the reaction vessel), adding grayscale values for those images to a database, and then retrieving those grayscale values when it was time to obtain 2002 the particle mix turbidity data. The sandwich assay and particle mix turbidity data could then be checked 2003 for correlations. If such correlations existed, then they could be used to trigger appropriate remediations 2006 for the analyzer. For example, if the images indicated lower turbidity (i.e., lighter grayscale values) at the particle mixing stage of an assay correlated with lower signal strength for the sandwich QC materials, this could be treated as indicating an issue that should be addressed by replacing a probe used by the analyzer at the particle mixing stage. Similarly, if the images indicated lower turbidity at a substrate dispensing position on the wash wheel correlated with lower signal strength for the sandwich QC materials, this could be treated as indicating an issue that should be addressed by replacing a probe used by the analyzer to mix reaction vessel contents at the reaction mix stage of an assay. Alternatively, if no correlations were found, a method such as shown in FIG. 13 could finish 2004, such as by sending a signal indicating that the trend analysis for a particular analyzer under consideration was complete.

Figure 6:
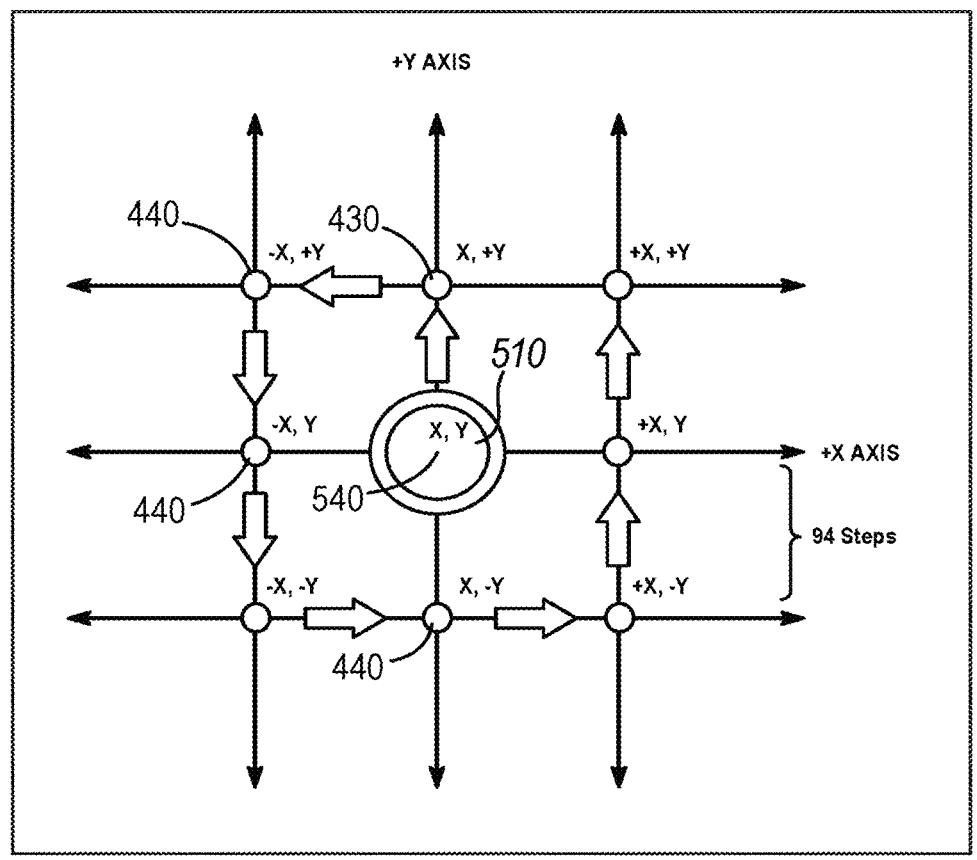
FIG. 6 is a schematic plan view of movements that could be used for alignment remediation in some embodiments.
Figure 7:
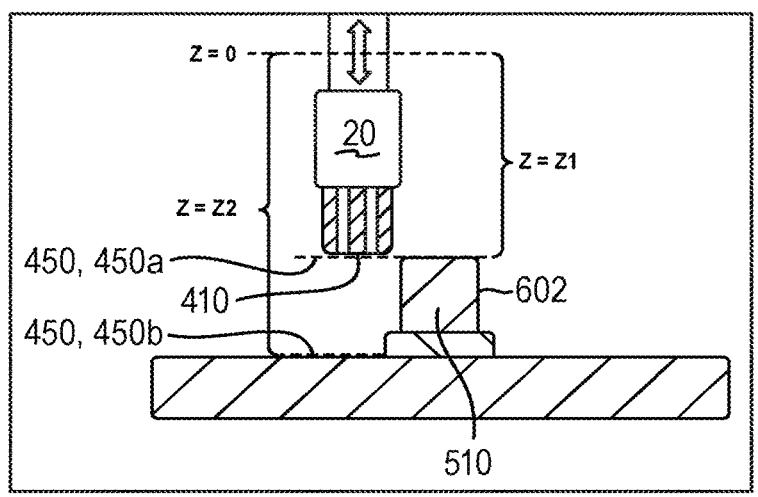
FIG. 7 is a schematic elevation view of movements associated with finding a presence of a target by detecting stalling of an actuator.

Turning now to FIGS. 6-9, those figures illustrate an approach to self-correcting alignment errors that could be performed in some embodiments. In such an approach, a target having a gripped portion 602 (e.g., a pin, a head) can be used to remedy gripper misalignments by placing the target at an area where the gripper would normally grip a vessel and then providing the gripper with commands that would normally cause it to engage with a vessel at that position if there was no misalignment. A test can then be performed to determine the actual position of the target relative to the gripper by testing for slippage along a vertical axis. This test can include moving an actuator of the griper in the Z axis direction such that the gripper 20 as shown in FIG. 7 is run against the target 510 or run against areas adjacent to the target 510. This Z axis test may be repeated around the assumed position of the target in a grid hunting fashion as shown in FIG. 6. Preferably, the actuator for the gripper will include a stepper motor and an encoder, and by comparing the difference reported by the stepper motor and the encoder, it may be determined if slippage has occurred in the stepper motor. The stepper motor may be operated at a reduced power level to make slippage occur at a lower force magnitude than would occur in normal operation of the actuator.

If the slippage is not detected in a certain range, it is determined that the gripper 20 has missed the target 510 and grid hunting may resume, as illustrated at FIG. 6. For example, if the gripper 20 has missed the target 510 at the X, Y position, a new attempt may be made at the X, +Y position. Likewise, if the target 510 is missed again, a third try may be made at the −X, +Y position. In some embodiments, the gripper 20 will be moved until all nine positions have been checked. In other embodiments, more than nine positions may be checked or fewer than nine positions may be checked. In other embodiments, the X Y coordinates may not necessarily be rectilinear as illustrated at FIG. 6.

Figure 8:
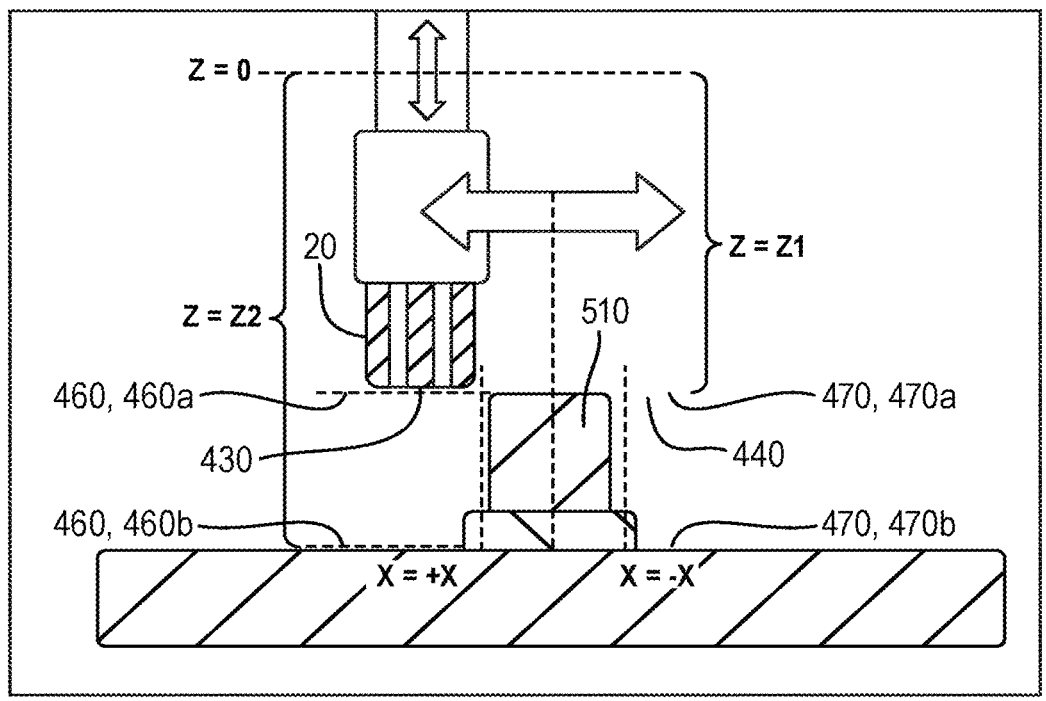
FIG. 8 is a schematic elevation view of movements that may be used to determine edges of a target.

FIG. 7 illustrates the gripper 20 being positioned at a first position near the top of the target 510. Upon testing for Z axis stalling, a first stalled position 450 will be detected. If the first stalled position is at 450a then the gripper assembly (which may also be referred to as a vessel holding assembly) 20 has met the top of the target 510. If the first stalled position 450 is at 450b, then the target 510 has been missed. A first predetermined position 410 is thereby indicated at position X, Y of FIG. 6 at an elevation indicated at FIG. 7. Upon the gripper 20 missing the target 510 at position X, Y, the gripper 20 is moved to position 430, as illustrated at FIG. 8. If position 430 also results in the gripper 20 missing the target 510, the gripper 20 is moved to subsequent predetermined positions 440 until the target 510 is found. As illustrated at FIG. 8, a second stalled position 460 may be at 460a, in which the gripper 20 has detected a top of the target 510. However, if the second stalled position 460 is 460b, then the target 510 has again been missed. Upon missing the target at the third predetermined position 430, the gripper 20 is moved toward the subsequent predetermined positions 440 and the stalling test is repeated. As further illustrated at FIG. 8, the gripper may stall at the subsequent stalled position 470a which indicates the top of the target 510 has been detected. However, if the subsequent stalled positions 470 are at 470b, the target 510 has again been missed and additional subsequent predetermined positions, as illustrated at FIG. 6 will be tested until the target 510 is found.

Figure 9:
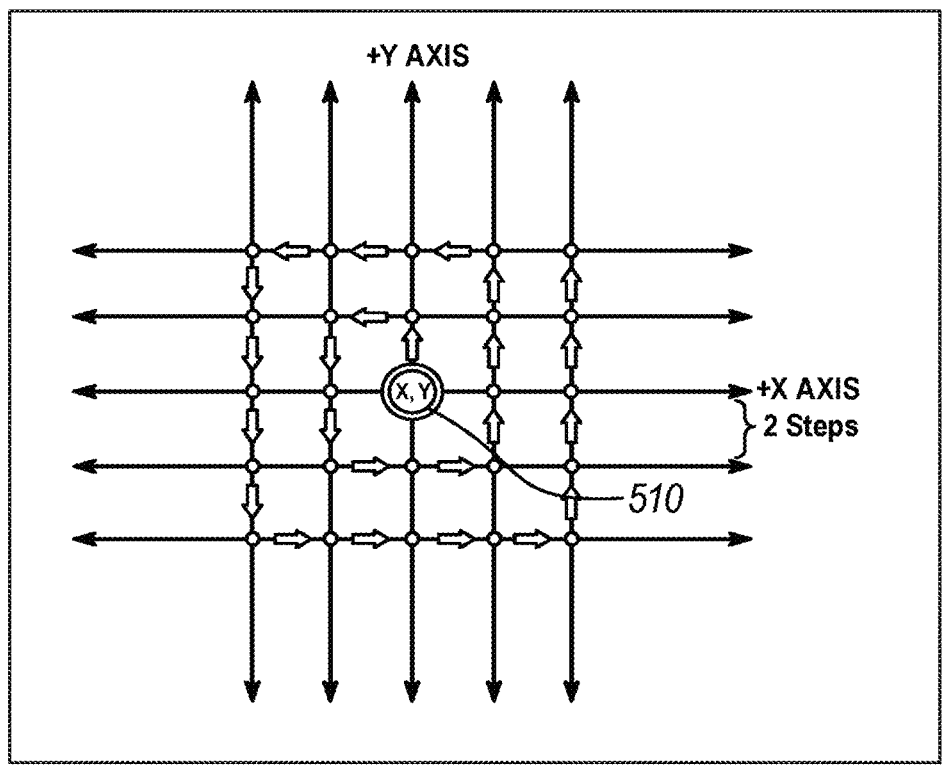
FIG. 9 is a schematic plan view of movements associated with testing a grip pattern.

Upon the target 510 being found, Z axis slippage is again used to discover the boundaries of the target 510. In particular, the edges of the target are located. This may also be done in a grid hunting fashion, as illustrated at FIG. 9. The increments used in the edge detecting grid hunting may be substantially smaller than the increments used in the initial pin detection grid hunting. Once the edges are discovered for the +X and −X limits, then the center 540 should be calculated along the X direction. This may be repeated for the +Y and −Y limits or +a and −a limits. After calculating centers for both directions, the gripper 20 should be moved to the center position 540 and tested to see if it can reach a proper Z height while holding the target. If so, then the actual position of the target will be treated as having been successfully detected, and the difference between that actual position and the position the target would have been expected to occupy if there had been no misalignment could be used to modify the movement of the gripper going forward to compensate for the misalignment.

Figure 15:
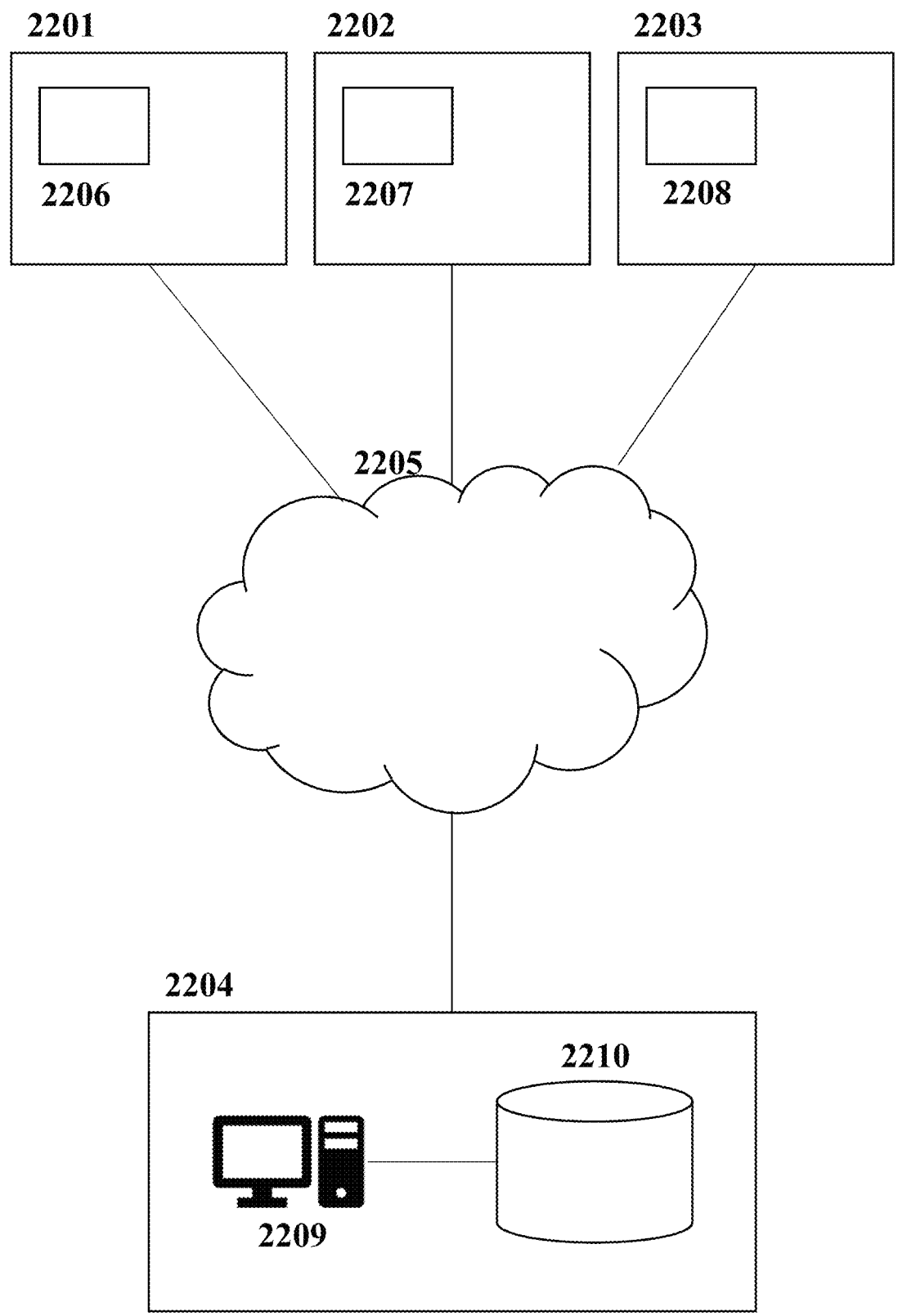
FIG. 15 illustrates an exemplary environment in which aspects of the disclosed technology may be deployed.

Turning now to FIG. 15, that figure illustrates an exemplary environment in which aspects of the disclosed technology may be deployed. In that environment, a plurality of laboratories 2201 2202 2203 are connected to a remote maintenance system 2204 via a network 2205. Within each of the laboratories 2201 2202 2203, there is disposed a diagnostic instrument 2206 2207 2208 instrument with various sensors such as the temperature sensors and cameras described previously. Within the remote maintenance system 2204, there is an analysis server 2209 and a database 2210. In operation, the diagnostic instruments 2206 2207 2208 would send QC test results and information gathered by their sensors to the remote maintenance system 2204 where it would be stored in the database 2210 and processed using a processor from the analysis server 2209, such as to perform trend analysis as described previously in the context of FIGS. 5 and 10-13. The results of this analysis could then be communicated back to the relevant laboratory (e.g., to cause an alert to appear on a user interface of a computer at the laboratory), to a field service engineer, to both, or to neither (e.g., if there were components identified as at risk for incipient failure in the trend analysis) as appropriate in a particular context.

Of course, it should be understood that modifications on the environment of FIG. 15 may also be possible. For example, in some contexts, trend analysis may be performed using computers at the relevant laboratories 2201 2202 2203, rather than a remote maintenance server 2209 as illustrated in the environment of FIG. 15. In these types of scenarios, the remote maintenance system 2204 may be entirely eschewed, or it may be included, but only in a limited capacity. For instance, a remote maintenance system 2204 may be included, but it may be limited to analyzing correlations which were identified but not connected with any particular types of component issues to determine potential updates to rules used in performing trend analysis. Other types of modifications are also possible, and will be immediately apparent to those of ordinary skill in the art in light of this disclosure. Accordingly, the exemplary environment of FIG. 15, should be understood as being illustrative only, and should not be treated as limiting.

It should also be understood that variations on the examples and embodiments described above are also possible in aspects other than the types of environments in which the disclosed technology may be deployed. For example, while FIGS. 5 and 10-13 and the accompanying discussion of those figures described moving to "next" trend analysis, in different embodiments, various types of trend analysis may be performed in any order, and/or different types of trend analysis may be performed than those explicitly illustrated in FIGS. 5 and 10-13 and described in the associated text. As another example of a type of variation that may be present in some embodiments, while trend analysis methods such as shown in FIG. 5 illustrated identifying 1203 correlations and then checking 1205 any identified correlations against temperature sensitivity rules. However, in some embodiments, it is possible that correlations may only be checked for time series information for QC materials that had previously been identified as materials where a correlation between those materials' results and temperature data, and a subsequent step of checking correlations against rules could be omitted.

Another example of a type of variation that may exist between embodiments is in relations between analysis that could identify root causes of failures (e.g., as described in the context of FIG. 4) and analysis that could identify incipient failures (e.g., as described in the context of FIGS. 5 and 10-13). For instance, while some embodiments may include both analysis to identify root causes of failures and analysis to identify incipient failures, other embodiments may include only analysis to identify root causes of failures, or only analysis to identify incipient failures. Similarly, while some embodiments may perform trend analysis only when there are no failures when analyzing a set of quality control materials, other embodiments may continuously or periodically perform trend analysis regardless of whether there was or wasn't a failure of quality control tests. It is also possible that, in some cases, root cause analysis such as shown in FIG. 4 could be used for failed tests from a single run of quality control tests, while trend analysis such as shown in FIGS. 5 and 10-13 could be performed for the QC tests whose results did not themselves indicate failures.

Another example of a type of variation that may exist between embodiments is in reactions to a failed quality control result. For example, in some cases, if a quality control test fails, rather than directly checking 1104 against device diagnostic rules as shown in FIG. 4, one or more confirmation steps may be performed. These steps could include repeating the failed quality control test, repeating the failed quality control test after recalibrating the analyzer, and/or repeating the quality control test with a different lot.

It should be understood that, while various embodiments and variations thereon have been provided, those embodiments and variations are intended to be illustrative, and that other variations and embodiments will be immediately apparent to, could easily be implemented without undue experimentation by, those of ordinary skill in the art in light of this disclosure. For example, while FIG. 2 illustrated how a subset of assays for use in checking for component failures could be generated, other approaches are possible. For example, in some cases, such a subset could be generated by treating definition of the subset as an instance of the set cover problem or the minimum test collection problem with a universe modeled using the components of the analyzer. In such a case, the subset could be generated by creating an approximate solution to the modeled problem, such as using a greedy algorithm. Similarly, in some embodiments, it may be possible to increase the efficiency of quality control testing even if it is not possible to identify a subset of assays covering all components of an analyzer, such as by performing testing using less than all concentrations of quality control materials when the test is intended to identify component failures. Other modifications are also possible, and will be immediately apparent to those of ordinary skill in the art. Accordingly, the protection provided by this document or any related document should be understood as being defined by the claims in such document when the terms in those claims are given their broadest reasonable interpretations as provided by a general purpose dictionary, except where an explicit definition for such terms is provided under an "Explicit Definitions" heading.

Explicit Definitions

When used in the claims, "based on" should be understood to mean that something is determined at least in part by the thing that it is indicated as being "based on." For a claim to indicate that something must be completely determined based on something else, it will be described as being "based EXCLUSIVELY on" whatever it is completely determined by.

When used in the claims "computer readable medium" should be understood to refer to any object, substance, or combination of objects or substances, capable of storing data or instructions in a form in which they can be retrieved and/or processed by a device. A computer readable medium should not be limited to any particular type or organization, and should be understood to include distributed and decentralized systems however they are physically or logically disposed, as well as storage objects of systems which are located in a defined and/or circumscribed physical and/or logical space. A reference to a "computer readable medium" being "non-transitory" should be understood as being synonymous with a statement that the "computer readable medium" is "tangible", and should be understood as excluding intangible transmission media, such as a vacuum through which a transient electromagnetic carrier could be transmitted. Examples of "tangible" or "non-transitory" "computer readable media" include random access memory (RAM), read only memory (ROM), hard drives and flash drives.

When used in the claims, "greedy algorithm" should be understood as referring to an algorithm that takes the best immediate or local solution while finding an answer to a problem.

When used in the claims, "means for determining a component covering subset" should be understood as a means plus function limitation where the function is "determining a component covering subset" and the corresponding structure is a computer configured to perform algorithms as illustrated in steps 204-207 of FIG. 2 and described in paragraphs 45-49 and 58 of this document.

When used in the claims, "quality control" should be understood as an aspect of the quality assurance process that consists of activities employed in detection and measurement of the variability in the characteristics of output attributable to the production system, specifically in this case in a laboratory on a diagnostic system/instrument, and may include corrective responses.

When used in the claims, "set" should be understood as a group of one or more elements of similar nature, design or function.

When used in the claims, "subset" should be understood as a set whose elements are all elements of the other set that the "subset" is identified as a subset of.

The invention claimed is:

1. A method comprising:
   a) performing a first test on a diagnostic instrument, wherein:
      i) the diagnostic instrument comprises a plurality of components and a plurality of assays;
      ii) the first test comprises determining if there has been a failure in an assay from a set of assays used by the diagnostic instrument to evaluate samples by performing steps comprising obtaining a first number of measurements by, for each assay in the set of assays, measuring each sample in a set of samples of a test material corresponding to that assay; and
   b) performing a second test on the diagnostic instrument, wherein the second test comprises determining if there has been a failure in a component from the plurality of components by performing steps comprising obtaining a second number of measurements by, for each assay in a subset of the set of assays, measuring at least one sample in the set of samples of the test material corresponding to that assay.

2. The method of claim 1, wherein the subset of the set of assays has a cardinality different from a cardinality of the set of assays.

3. The method of claim 1, wherein:
a) the first test and the second test are both quality control tests; and
b) each test material is a quality control material.

4. The method of claim 3, wherein the method comprises:
a) periodically performing quality control tests on the diagnostic instrument which comprise obtaining the first number of measurements, wherein each quality control test on the diagnostic instrument that comprises obtaining the first number of measurements is separated from a most recent preceding quality control test on the diagnostic instrument that comprises obtaining the first number of measurements by at least a first time period; and
b) periodically performing quality control tests on the diagnostic instrument which comprise obtaining the second number of measurements, wherein each quality control test on the diagnostic instrument that comprises obtaining the second number of measurements is separated from a most recent preceding quality control test on the diagnostic instrument that comprises obtaining the second number of measurements by less than the first time period.

5. The method of claim 1, wherein the subset of the set of assays is defined by:
a) using the plurality of components to model a universe for a problem, wherein the problem is:
i) a set cover problem; and
ii a minimum test collection problem;
and
b) generating an approximate solution for the problem.

6. The method of claim 5, wherein the problem is the minimum test collection problem.

7. The method of claim 1, wherein for each assay in the set of assays, the set of samples of the test material corresponding to that assay comprises:
i) a first sample having a first concentration of the test material;
ii) a second sample having a second concentration of the test material; and
iii) a third sample having a third concentration of the test material.

8. A method comprising:
a) receiving a set of parameters, wherein each parameter from the set of parameters is obtained based on performing a measurement of a corresponding sample that corresponds to that parameter on a diagnostic instrument that comprises a plurality of components;
b) identifying an issue for a particular component from the plurality of components based on analysis of at least two parameters from the set of parameters; and
c) executing a remediation action for the particular component based on identifying the issue for the particular component.

9. The method of claim 8, wherein each parameter from the set of parameters is related to quality control.

10. The method of claim 8, wherein:
a) the set of parameters comprises:
i) a failed quality control result outside an acceptance tolerance for the diagnostic instrument;
ii) a successful quality control result within the acceptance tolerance for the diagnostic instrument;
b) identifying the issue for the particular component is performed by determining that the particular component is a likely root cause for the failed quality control result based on:
i) determining that the corresponding sample for the failed quality control result was for an assay previously identified as susceptible to failures in the particular component; and
ii) determining that the corresponding sample for the successful quality control result was for an assay not previously identified as susceptible to failures in the particular component.

11. The method of claim 8, wherein:
a) each parameter from the set of parameters is a quality control result;
b) the set of parameters does not comprise any quality control results outside an accepted tolerance for the diagnostic instrument; and
c) identifying the issue for the particular component from the plurality of components is performed based on identifying a pattern with the set of parameters.

12. The method of claim 11, wherein:
a) the diagnostic instrument comprises a case and a set of one or more temperature sensors disposed inside the case;
b) identifying the pattern with the set of parameters comprises identifying a correlation between:
i) temperature data captured by the set of one or more temperature sensors; and
ii) two or more parameters from the set of parameters whose corresponding samples were for an assay previously identified as susceptible to temperature control failures in the particular component.

13. The method of claim 11, wherein:
a) for each parameter from the set of parameters, the corresponding sample for that parameter is a quality control sample;
b) the diagnostic instrument is configured to, for each quality control sample on which it performs a measurement, capture a test number for that quality control sample within a reagent pack; and
c) identifying the pattern with the set of parameters comprises identifying a correlation between:
i) test numbers for parameters corresponding to samples for assays previously identified as hard to suspend; and
ii) parameters corresponding to samples for assays previously identified as hard to suspend.

14. The method of claim 11, wherein:
a) the diagnostic instrument comprises a luminometer and is configured to capture substrate blank measurements comprising values obtained when vessels containing substrate adapted to generate chemiluminescent light in the presence of ALP are placed in the luminometer and measured without adding ALP;
b) identifying the pattern with the set of parameters comprises identifying a correlation between:
i) substrate blank measurements; and
ii) parameters corresponding to samples for sandwich assays.

15. The method of claim 11, wherein:
a) the set of parameters comprises:
i) a first quality control result, wherein the first quality control result corresponds to a quality control sample at a first concentration for an assay previously identified as susceptible to failures in the particular component;
ii) a second quality control result, wherein:
A) the second quality control result corresponds to a quality control sample at a second concentration for the assay previously identified as susceptible to failures in the particular component; and
B) the second concentration is greater than the first concentration; and
iii) a third quality control result, wherein:
A) the third quality control result corresponds to a quality control sample at a third concentration for the assay previously identified as susceptible to failures in the particular component; and
B) the third concentration is greater than the second concentration;
b) identifying the pattern with the set of parameters comprises calculating a projected result line for the assay previously identified as susceptible to failures in the particular component based on:
i) the first quality control result;
ii) the second quality control result;
iii) a first expected value, wherein the first expected value is based on lower and upper signal levels for the quality control sample at the first concentration for the assay previously identified as susceptible to failures in the particular component; and
iv) a second expected value, wherein the second expected value is based on lower and upper signal levels for the quality control sample at the second concentration for the assay previously identified as susceptible to failures in the particular component; and
c) identifying the issue for the particular component is performed by determining that the third quality control result does not match a value predicted based on:
i) lower and upper signal levels for the quality control sample at the third concentration for the assay previously identified as susceptible to failures in the particular component; and
ii) the projected result line.

16. The method of claim 11, wherein:
a) the diagnostic instrument comprises a wash wheel and a set of one or more cameras disposed proximate the wash wheel;
b) identifying the pattern with the set of parameters comprises identifying a correlation between:
i) parameters for samples corresponding to sandwich assays; and
ii) grayscale values derived from images of vials containing the samples corresponding to the sandwich assays captured by the set of one or more cameras disposed proximate the wash wheel.

17. The method of claim 8, wherein:
a) the method further comprises determining if there has been a failure in an assay from a set of assays used by the diagnostic instrument to evaluate samples by performing steps comprising obtaining a first number of measurements by, for each assay in the set of assays, measuring each sample in a set of samples of a test material corresponding to that assay; and
b) each parameter from the set of parameters is obtained based on performing the measurement of the corresponding sample that corresponds to that parameter using an assay from a subset of the set of assays.

18. The method of claim 8, wherein:
a) receiving the set of parameters comprises:
i) receiving sandwich assay quality control results; and
ii) obtaining turbidity data for reaction vessels after quality control assays had been added to those vessels during an analytic process; and
b) identifying the issue for the particular component from the plurality of components comprises checking for a correlation between the turbidity data and the sandwich assay quality control results.

19. A non-transitory computer readable medium storing instructions operable to configure a computer to perform a method comprising:
a) receiving a set of parameters, wherein the set of parameters comprises a first quality control result corresponding to a quality control sample for an assay identified as susceptible to failures in a particular component of a diagnostic instrument; and
b) identifying an issue for a particular component from a plurality of components comprised by the diagnostic instrument based on analysis of at least two parameters from the set of parameters, wherein the at least two parameters from the set of parameters comprises the first quality control result.

20. The computer readable medium of claim 19, wherein:
a) each parameter from the set of parameters is a quality control result;
b) the set of parameters does not comprise any quality control results outside an accepted tolerance for the diagnostic instrument;
c) the first quality control result corresponds to the quality control sample at a first concentration;
d) identifying the issue for the particular component from the plurality of components comprises identifying a pattern with the set of parameters;
e) the set of parameters comprises:
i) a second quality control result, wherein:
C) the second quality control result corresponds to a quality control sample at a second concentration for the assay previously identified as susceptible to failures in the particular component; and
D) the second concentration is greater than the first concentration; and
ii) a third quality control result, wherein:
A) the third quality control result corresponds to a quality control sample at a third concentration for the assay previously identified as susceptible to failures in the particular component; and
B) the third concentration is greater than the second concentration;
f) identifying the pattern with the set of parameters comprises calculating a projected result line for the assay previously identified as susceptible to failures in the particular component based on:
i) the first quality control result;
ii) the second quality control result;
iii) a first expected value, wherein the first expected value is based on lower and upper signal levels for the quality control sample at the first concentration for the assay previously identified as susceptible to failures in the particular component; and
iv) a second expected value, wherein the second expected value is based on lower and upper signal levels for the quality control sample at the second concentration for the assay previously identified as susceptible to failures in the particular component;

and
g) identifying the issue for the particular component is performed by determining that the third quality control result does not match a value predicted based on:
  i) lower and upper signal levels for the quality control sample at the third concentration for the assay previously identified as susceptible to failures in the particular component; and
  ii) the projected result line.
21. The computer readable medium of claim 19, wherein:
a) the method the instructions stored on the computer readable medium are operable to configure the computer to perform comprise determining if there has been a failure in an assay from a set of assays used by the diagnostic instrument to evaluate samples by performing steps comprising obtaining a first number of measurements by, for each assay in the set of assays, measuring each sample in a set of samples of a test material corresponding to that assay; and
b) each parameter from the set of parameters is obtained based on performing a measurement using a corresponding assay from a subset of the set of assays.

* * * * *